United States Patent
Watanabe et al.

(10) Patent No.: US 11,744,555 B2
(45) Date of Patent: Sep. 5, 2023

(54) ULTRASOUND SIGNAL PROCESSING DEVICE, ULTRASOUND DIAGNOSTIC DEVICE, AND ULTRASOUND SIGNAL PROCESSING METHOD

(71) Applicant: Konica Minolta, Inc., Tokyo (JP)

(72) Inventors: Yasuhito Watanabe, Takatsuki (JP); Junko Yoshida, Amagasaki (JP)

(73) Assignee: KONICA MINOLTA, INC., Tokyo (JP)

(*) Notice: Subject to any disclaimer, the term of this patent is extended or adjusted under 35 U.S.C. 154(b) by 490 days.

(21) Appl. No.: 16/460,092

(22) Filed: Jul. 2, 2019

(65) Prior Publication Data
US 2020/0015787 A1    Jan. 16, 2020

(30) Foreign Application Priority Data
Jul. 13, 2018  (JP) .................. 2018-133457

(51) Int. Cl.
*A61B 8/08*    (2006.01)
*A61B 8/14*    (2006.01)
(Continued)

(52) U.S. Cl.
CPC .......... *A61B 8/5207* (2013.01); *A61B 8/14* (2013.01); *A61B 8/4444* (2013.01);
(Continued)

(58) Field of Classification Search
CPC ....... A61B 8/5207; A61B 8/14; A61B 8/4477; A61B 8/5223; A61B 8/4444;
(Continued)

(56) References Cited

U.S. PATENT DOCUMENTS

| | | | |
|---|---|---|---|
| 6,193,659 B1* | 2/2001 | Ramamurthy | A61B 8/481 600/443 |
| 2016/0120503 A1* | 5/2016 | Tsushima | A61B 8/5207 367/7 |

(Continued)

FOREIGN PATENT DOCUMENTS

| | | |
|---|---|---|
| JP | 2014183934 A | 10/2014 |
| JP | 2016087453 A | 5/2016 |
| JP | 2018093974 A | 6/2018 |

*Primary Examiner* — Christopher Koharski
*Assistant Examiner* — Sean A Frith
(74) *Attorney, Agent, or Firm* — LUCAS & MERCANTI, LLP

(57) ABSTRACT

An ultrasound signal processing device performs transmission events by an ultrasound probe having transducer elements, generates a sub-frame acoustic line signal for each transmission event based on reflected ultrasound, and synthesizes sub-frame acoustic line signals to generate a frame acoustic line signal. A transmitter causes the ultrasound probe to transmit ultrasound beams to an ultrasound main irradiation area. A receiver generates receive signals for the transducer elements. A delay-and-sum calculator sets a target area in the ultrasound main irradiation area, and performs delay-and-sum calculation with respect to the receive signals from measurement points in the target area to generate a sub-frame acoustic line signal. The target area has, in a depth range shallower than a focal point, a width in the transducer element array direction that decreases as the depth decreases. A synthesizer synthesizes sub-frame acoustic line signals.

14 Claims, 24 Drawing Sheets

(51) Int. Cl.
*A61B 8/00* (2006.01)
*G01S 15/89* (2006.01)

(52) U.S. Cl.
CPC ........... *A61B 8/4477* (2013.01); *A61B 8/4488* (2013.01); *A61B 8/4494* (2013.01); *A61B 8/5223* (2013.01); *G01S 15/8915* (2013.01)

(58) Field of Classification Search
CPC . A61B 8/4494; A61B 8/4488; G01S 15/8915; G01S 15/8997; G01S 7/52046; G01S 7/52085
See application file for complete search history.

(56) References Cited

U.S. PATENT DOCUMENTS

| 2017/0128038 | A1* | 5/2017 | Tsushima | A61B 8/5207 |
| 2018/0055486 | A1* | 3/2018 | Tsushima | G01S 15/8927 |
| 2018/0228462 | A1* | 8/2018 | Maghsoudnia | G01F 22/00 |

* cited by examiner

ULTRASOUND SIGNAL PROCESSING DEVICE, ULTRASOUND DIAGNOSTIC DEVICE, AND ULTRASOUND SIGNAL PROCESSING METHOD

This application claims priority to Japanese Patent Application No. 2018-133457 filed Jul. 13, 2018, the contents of which are hereby incorporated herein by reference in their entirety.

BACKGROUND

Technical Field

The present disclosure relates to ultrasound signal processing devices and ultrasound diagnostic devices equipped with the same, and particularly to receive beam forming in ultrasound signal processing devices.

Description of the Related Art

An ultrasound diagnostic device transmits ultrasound to the inside of a subject via an ultrasound probe (hereinafter also referred to as a probe), and receives reflected ultrasound (echoes) caused by a difference in acoustic impedance of tissue in the subject. Further, the ultrasound diagnostic device generates an ultrasound tomographic image representing structure of internal tissue of the subject based on electric signals acquired through reception of the reflected ultrasound, and displays the ultrasound tomographic image on a monitor (hereinafter also referred to as a display). Ultrasound diagnostic devices are widely used for morphological diagnoses of living bodies, for having low invasiveness and achieving real-time observation of tissues through tomographic images and the like.

A typical method applied in conventional ultrasound diagnostic devices for forming signals based on received reflected ultrasound (i.e., receive beam forming) is delay-and-sum beam forming. According to this method, transmission beam forming (i.e., transmission of ultrasound by a plurality of transducer elements towards the inside of a subject) is typically performed such that a transmitted ultrasound beam converges (focuses) at a predetermined focal depth inside the subject. Further, according to this method, measurement points are always set along the central axis of the transmitted ultrasound beam. Due to this, one ultrasound transmission event generates only one or a few acoustic line signals along the central axis of the transmitted ultrasound beam, and thus reflected ultrasound is not utilized in an efficient manner. In addition, with this method, it is also problematic that an acoustic line signal acquired from a measurement point distant from the transmission focal point has low spatial resolution and S/N ratio.

Meanwhile, a receive beam forming method is being proposed that utilizes a so-called synthetic aperture method to yield images with high spatial resolution and high quality not only from near the transmission focal point but also from areas other than near the transmission focal point. One example of receive beam forming utilizing the synthetic aperture method can be found disclosed in Japanese Patent Application Publication No. 2016-87453. According to this method, delaying is performed taking into consideration both the time amount required for ultrasound to arrive at a measurement point and the time amount required for reflected ultrasound from the measurement point to arrive at a transducer element. Thus, the method achieves receive beam forming making use of not only reflected ultrasound from an area of an ultrasound main irradiation area near the transmission focal point but also reflected ultrasound from areas of the ultrasound main irradiation area other than the area near the transmission focal point. Due to this, the method enables generating, from one ultrasound transmission event, acoustic line signals covering the entire ultrasound main irradiation area, including areas far from the transmission focal point. Note that in the present disclosure, an ultrasound main irradiation area is an area such that at every point in the ultrasound main irradiation area, ultrasound transmitted from transducer elements composing a transmission transducer element array is in-phase. In addition, the synthetic aperture method enables setting a virtual transmission focal point with respect to each measurement point based on multiple receive signals acquired for the same measurement point through multiple transmission events. Thus, the synthetic aperture method enables acquiring an ultrasound image with higher spatial resolution and higher S/N ratio.

SUMMARY

In the synthetic aperture method, for efficient use of ultrasound and high resolution, it is preferable that an area for which acoustic line signals for a single transmission event are generated (hereinafter referred to as a target area) should have large size, and it is further preferable that the entire ultrasound main irradiation area should be used as the target area. However, in shallow areas around a probe, even the synthetic aperture method sometimes cannot sufficiently solve a problem that acoustic line signals acquired from measurement points distant from the central axis of transmitted ultrasound beam have low spatial resolution and S/N ratio. On the other hand, in the case where only areas around the central axis of transmitted ultrasound beam are set as a target area, a small number of reception signals corresponds to the same measurement point and thus the synthetic aperture method has difficulty in improving spatial resolution and S/N ratio.

One aspect of the present disclosure has been made in view of the above problem, and aims to provide an ultrasound signal processing device and an ultrasound signal processing method that enable suppressing decrease in spatial resolution and S/N ratio irrespective of the depth of measurement points by the synthetic aperture method, and to provide an ultrasound diagnostic device using the same.

An ultrasound signal processing device pertaining to at least one aspect of the present disclosure is an ultrasound signal processing device that performs transmission events of transmitting ultrasound beams to a subject by using an ultrasound probe having transducer elements, generates a sub-frame acoustic line signal for each of the transmission events based on signals acquired through reception of reflected ultrasound from the subject by the ultrasound probe, and synthesizes sub-frame acoustic line signals for the respective transmission events to generate a frame acoustic line signal. The ultrasound signal processing device includes ultrasound signal processing circuitry including: a transmitter that, for each of the transmission events, shifts a transmission aperture including part of the transducer elements in a transducer element array direction in which the transducer elements are arrayed, and causes the ultrasound probe to transmit ultrasound beams to an ultrasound main irradiation area defined by a position of the transmission aperture; a receiver that, for each of the transmission events, generates sequences of receive signals for at least part of the transducer elements based on reflected ultrasound received by the ultrasound probe from the subject; a delay-and-sum calculator that, for each of the transmission events, sets a target area in the ultrasound main irradiation area, and performs delay-and-sum calculation with respect to the sequences of receive signals from measurement points located in the target area to generate a sub-frame acoustic line signal, the target area having, in a depth range shallower than a focal point, a width in the transducer element array direction that decreases as the depth decreases; and a synthesizer that synthesizes sub-frame acoustic line signals for the transmission events to generate a frame acoustic line signal.

BRIEF DESCRIPTION OF THE DRAWINGS

The advantages and features provided by one or more embodiments of the disclosure will become more fully understood from the detailed description given hereinbelow and the appended drawings which are given by way of illustration only, and thus are not intended as a definition of the limits of the present invention.

In the drawings.

DETAILED DESCRIPTION

Hereinafter, one or more embodiments of the present disclosure will be described with reference to the drawings. However, the scope of the invention is not limited to the disclosed embodiments.

<How Inventors Arrived at Aspects of Present Invention>

The inventors found a problem that ultrasound diagnostic devices deploying the synthetic aperture method have spatial resolution and S/N ratio of acoustic line signals (hereinafter also referred to as acoustic line signal quality) that are low in shallow areas.

According to the synthetic aperture method, firstly, a target area is set for each transmission event, and receive transducer elements Rk are set for each measurement point in the target area, receiving reflected ultrasound from the measurement point. Then, a reception signal is generated for each measurement point based on reflected ultrasound received by receive transducer elements Rk corresponding to the measurement point, and delay-and-sum calculation with respect to reception signals is performed to generate an acoustic line signal, thereby generating a sub-frame acoustic line signal for one transmission event. Then, sub-frame acoustic line signals are synthesized on the basis of positions of measurement points, thereby generating a frame acoustic line signal. This achieves virtual transmission focusing.

Figure 14A:
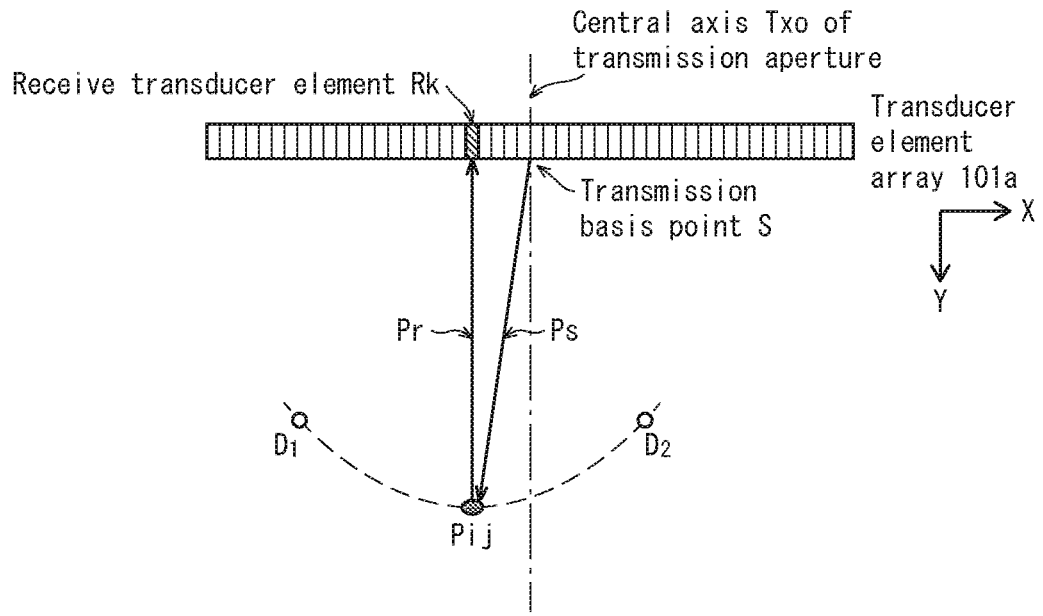
FIGS. 14A and 14B are schematics illustrating relationship between S/N ratio and positional relationship between a transmission aperture Tx and a measurement point Pij.
Figure 14B:
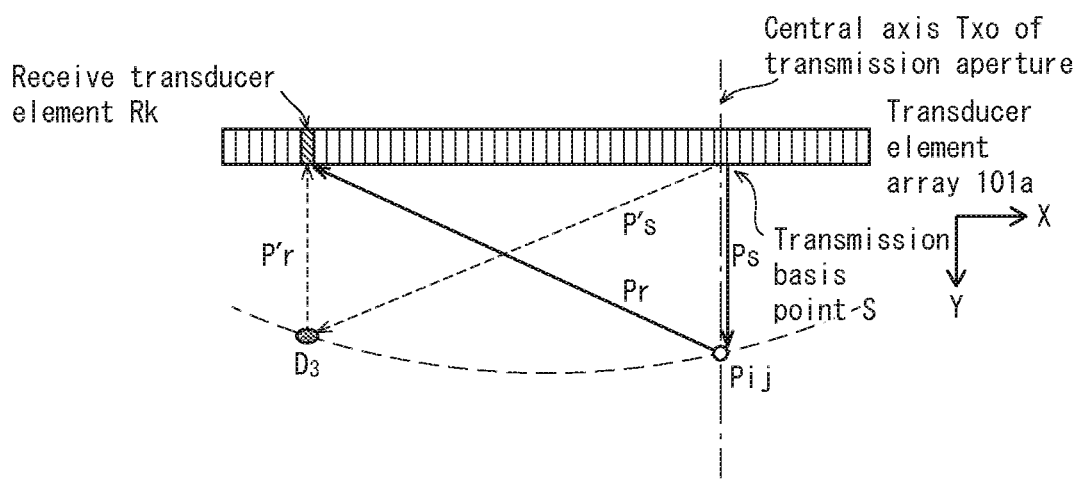

However, the inventors found a problem that, with respect to measurement points located at shallow depths, spatial resolution and S/N ratio of acoustic line signals decrease for measurement points located distant from the central axis of a transmitted ultrasound beam. The following provides detail description with reference to FIGS. 14A and 14B. FIGS. 14A and 14B schematically illustrate a path along which an ultrasound beam transmitted from a transducer element array 101a arrives at a measurement point Pij, and reflected ultrasound from the measurement point Pij arrives at a receive transducer element Rk. Here, a surface of an ultrasound probe that contacts a subject has an area corresponding to transducer elements used for ultrasound beam transmission, and this area is defined as a transmission aperture. The center of the transmission aperture is defined as a transmission basis point S. Also, a straight line that passes through the transmission basis point S and is parallel to a travel direction of the ultrasound beam is defined as a central axis Txo of the transmission aperture. In the case where the ultrasound beam is plane wave, the central axis Txo of the transmission aperture is a straight line perpendicular to wavefront of the ultrasound beam. In contrast, in the case where the ultrasound beam is converging wave, the central axis Txo of the transmission aperture is a straight line that passes through the transmission basis point S and a focal point F. The transmission focal point F is located at a position where the ultrasound beam converges or the center of an area where the ultrasound beam converges. Here, the ultrasound beam is regarded as having traveled along a path Ps from the transmission basis point S to the measurement point Pij. Similarly, the reflected ultrasound is regarded as having traveled along a path Pr from the measurement point Pij to the receive transducer element Rk. Meanwhile, the receive transducer element Rk is specified based on the total of a time amount required for the ultrasound beam to travel along the path Ps to the measurement point Pij and a time amount required for the reflected ultrasound to travel along the path Pr from the measurement point Pij. In other words, it is impossible to distinguish, from the reflected ultrasound from the measurement point Pij, reflected ultrasound from a reference point D according to which the total length of a path P's from the transmission basis point S to the reference point D and a path P'r from the reference point D to the receive transducer element Rk is equal to the total length of the path Ps and the path Pr. Meanwhile, the reference point D is located on the circumference of an ellipse with foci at the transmission basis point S and the receive transducer element Rk. That is, the position of the reference point D depends on the position of the receive transducer element Rk. Thus, delay-and-sum calculation with respect to signals received by receive transducer elements Rk not only strengthens the reflected ultrasounds from the measurement point Pij but also adds the reflected ultrasound from the reference point D.

On the other hand, the degree to which the delay-and-sum calculation cancels the reflected ultrasound from the reference point D also depends on the position of the measurement point Pij. For example, as illustrated in FIG. 14A, in the case where the measurement point Pij is located around the central axis Txo of the transmission aperture, reflected ultrasound from the measurement point Pij is received most strongly by the receive transducer element Rk that is spatially closest to the measurement point Pij. Here, the transmission basis point S and the receive transducer element Rk are close to each other, and thus the reference point D is located on a circumference of an approximate circle with the center at the receive transducer element Rk. Meanwhile, transmitted ultrasound beam becomes stronger towards the central axis Txo of the transmission aperture, and thus ultrasound beam arriving at the measurement point Pij is stronger than ultrasound beams arriving at reference points $D_1$ and $D_2$. In other words, with respect to reception signals corresponding to the receive transducer element Rk, the reflected ultrasound from the measurement point Pij is the strongest. Thus, delay-and-sum calculation reduces influence of the reflected ultrasound from the reference point D thereby to improve spatial resolution and S/N ratio of acoustic line signals. Also, in the case where the measurement point Pij is located at a deep depth, a slight influence is exerted by the distance between the receive transducer element Rk and the transmission basis point S relative to the total length of the paths Ps and Pr, and thus delay-and-sum calculation similarly improves the spatial resolution and the S/N ratio of acoustic line signals. However, as illustrated in FIG. 14B, in the case where the receive transducer element Rk is distant from the measurement point Pij, the following problem occurs. The receive transducer element Rk receives reflected ultrasound from the measurement point Pij along the shortest route Pr. Here, the reference point D is located on a circumference of an ellipse with foci at the transmission basis point S and the receive transducer element Rk. Thus, with respect to reception signals corresponding to the receive transducer element Rk, no intensity difference exists between the reflected ultrasound from the measurement point Pij and reflected ultrasound from a reference point $D_3$. Also, there are a large number of reference points D in addition to the reference point $D_3$. Accordingly, delay-and-sum calculation cannot sufficiently strength the reflected ultrasounds from the measurement point Pij, thus sometimes leaving reflected ultrasounds from the reference points D including the reference point $D_3$. This causes a problem that the spatial resolution and the S/N ratio of acoustic line signals decrease due to the reflected ultrasounds from the reference points D.

The cause for the above problem of low spatial resolution and S/N ratio of acoustic line signals lies in the distance between the measurement point Pij and the central axis Txo of the transmission aperture. Thus, one conceivable method for solving this problem is to reduce the width of the target area in the transducer element array direction in order to exclude areas distant from the central axis Txo of the transmission aperture from the target area. However, such a reduction in width of the target area in the transducer element array direction results in size reduction of an overlap area between target areas of different transmission events. In particular, in areas other than shallow areas, the spatial resolution and the S/N ratio of acoustic line signals decrease due to decrease in the synthesizing number of acoustic line signals. In view of this, the inventors tried to find a method of improving the spatial resolution and the S/N ratio in shallow areas while suppressing the decrease in areas other than the shallow areas, and as a result arrived at embodiments of the present disclosure.

The following embodiment describes an ultrasound signal processing method and an ultrasound diagnostic device including the ultrasound signal processing method in detail, with reference to the accompanying drawings.

Embodiment 1

<Overall Structure>

The following describes an ultrasound diagnostic device 100 pertaining to an embodiment, with reference to the accompanying drawings.

Figure 1:
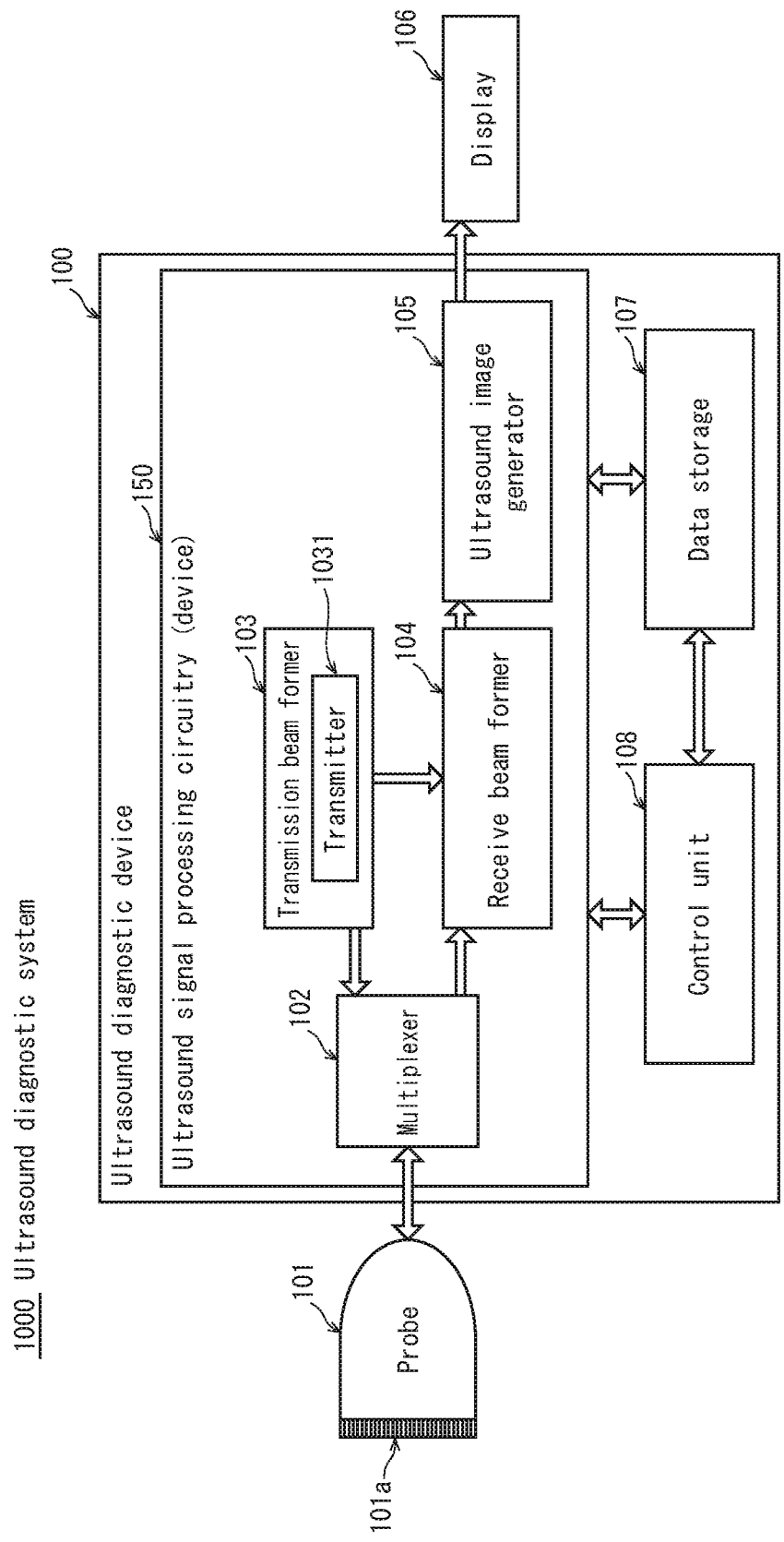
FIG. 1 is a functional block diagram illustrating the structure of an ultrasound diagnostic device 100 pertaining to an embodiment.

FIG. 1 illustrates functional blocks of an ultrasound diagnostic system 1000 pertaining to the embodiment. As illustrated in FIG. 1, the ultrasound diagnostic system 1000 includes a probe 101, the ultrasound diagnostic device 100, and a display unit 106. The probe 101 includes a plurality of transducer elements 101a. Each of the transducer elements 101a is capable of transmitting ultrasound towards the subject and receiving reflected ultrasound (echo signals). The ultrasound diagnostic device 100 causes the probe 101 to perform transmission/reception of ultrasound, and generates an ultrasound image based on signals output from the probe 101. The display unit 106 displays the ultrasound image on any display device provided thereto. The probe 101 and the display unit 106 are separately connectable to the ultrasound diagnostic device 100. FIG. 1 illustrates the ultrasound diagnostic device 100 with the probe 101 and the display unit 106 connected thereto. Alternatively, the ultrasound diagnostic device 100 may include therein the probe 101 and the display unit 106.

<Structure of Ultrasound Diagnostic Device 100>

The ultrasound diagnostic device 100 includes a multiplexer 102, a transmission beam former 103, and a receive beam former 104. The multiplexer 102 selects one or more of the transducer elements 101a for ultrasound transmission and one or more of the transducer elements 101a for ultrasound reception. The multiplexer 102 provides each of the transducer elements 101a for ultrasound transmission with input, and receives output from the transducer elements 101a for ultrasound reception. The transmission beam former 103 controls timings of application of a high voltage for ultrasound transmission to each of the transducer elements 101a for ultrasound transmission. The receive beam former 104 performs some amplification and A/D conversion on electric signals yielded by the transducer elements 101a for ultrasound reception, based on reflected ultrasound received by the probe 101, and performs receive beam forming to generate acoustic line signals. In addition, the ultrasound diagnostic device 100 includes an ultrasound image generator 105, a data storage 107, and a control unit 108. The ultrasound image generator 105 generates an ultrasound image (a B-mode image) based on signals output from the receive beam former 104. The data storage 107 stores the acoustic line signal output from the receive beam former 104 and the ultrasound image output from the ultrasound image generator 105. The control unit 108 controls each of the components of the ultrasound diagnostic device 100.

Among the components of the ultrasound diagnostic device 100, the multiplexer 102, the transmission beam former 103, the receive beam former 104, and the ultrasound image generator 105 constitute ultrasound signal processing circuitry 150, and the ultrasound signal processing circuitry 150 constitutes an ultrasound signal processing device.

The components of the ultrasound diagnostic device 100, for example, the multiplexer 102, the transmission beam former 103, the receive beam former 104, the ultrasound image generator 105, and the control unit 108 each may be implemented by using a hardware circuit such as a field-programmable gate array (FPGA) and an application-specific integrated circuit (ASIC). Alternatively, the components each may be implemented by using a combination of software and a programmable device such as a processor. As a processor, a central processing unit (CPU) or a graphics processing unit (GPU) may be used for example, and a construction using a GPU is referred to as a general-purpose computing on graphics processing unit (GPGPU). Each of such components may be implemented as one circuit component, or as an aggregate of a plurality of circuit components. Further, a plurality of such components may be implemented as one circuit component, or as an aggregate of a plurality of circuit components.

The data storage 107 is a computer-readable recording medium. For example, the data storage 107 may be implemented by using a flexible disk, a hard disk, an MO, a DVD, a DVD-RAM, a BD, or a semiconductor memory. Alternatively, the data storage 107 may be an external storage device connected to the ultrasound diagnostic device 100.

Note that the ultrasound diagnostic device 100 pertaining to the present embodiment need not have the structure illustrated in FIG. 1. For example, the ultrasound diagnostic device 100 need not include the multiplexer 102, and the transmission beam former 103 and the receive beam former 104 may be directly connected with each transducer element 101a of the probe 101. Further, the probe 101 may have built-in therein a part or the entirety of each of the transmission beam former 103, the receive beam former 104, and the like. Such modifications apply not only to the ultrasound diagnostic device 100 pertaining to the present embodiment, but also similarly apply to the ultrasound diagnostic devices described later in modifications in the present disclosure.

<Structure of Main Part of Ultrasound Diagnostic Device 100>

The ultrasound diagnostic device 100 pertaining to the present embodiment is characterized for including the transmission beam former 103 and the receive beam former 104. The transmission beam former 103 causes the transducer elements 101a of the probe 101 to transmit ultrasound beam. The receive beam former 104 receives electric signals acquired through the probe 101 receiving reflected ultrasound, performs computation with respect to the electric signals, and generates acoustic line signals for forming an ultrasound image. Accordingly, the present disclosure focuses on the structure and the functions of the transmission beam former 103 and the receive beam former 104. Note that components other than the transmission beam former 103 and the receive beam former 104 may have structures and functions similar to those in conventional ultrasound diagnostic devices. In other words, the ultrasound diagnostic device 100 may be implemented by replacing beam formers in a conventional ultrasound diagnostic device with the beam formers pertaining to the present embodiment.

The following describes the structure of the transmission beam former 103 and the receive beam former 104.

1. Transmission Beam Former 103

The transmission beam former 103 is connected to the probe 101 via the multiplexer 102. The transmission beam former 103 controls timings of application of high voltage with respect to each of a plurality of transducer elements 101a composing a transmission aperture Tx. The transmission aperture Tx is an array of transducer elements composed of all or some of the transducer elements 101a of the probe 101. Note that in the following, the term "transmission transducer element" is used to refer to transducer elements composing the transmission aperture Tx. The transmission beam former 103 includes a transmitter 1031.

The transmitter 1031 performs transmission processing. The transmission processing involves supplying a transmission signal having a pulsar waveform to each of the transmission transducer elements. A transmission transducer element receiving a transmission signal transmits an ultrasound beam. The transmitter 1031 supplies transmission signals to the transmission transducer elements based on transmission control signals output from the control unit 108. In specific, the transmitter 1031 includes, for example, a clock generation circuit, a pulse generation circuit, and a delay circuit. The clock generation circuit generates a clock signal specifying the transmission timing of ultrasound beams. The pulse generation circuit generates pulse signals for driving the transmission transducer elements. The delay circuit performs focus processing so that ultrasound beams are appropriately focused. In specific, the delay circuit sets a delay time for each transmission transducer element, and delays the transmission of the ultrasound beam from the transmission transducer element by the corresponding delay time.

The transmitter 1031 repetitively performs ultrasound transmission while shifting the transmission aperture Tx by a shift pitch Mp in the transducer element array direction each time, so that all of the transducer elements 101a of the probe 101 transmit ultrasound. In the present embodiment, the shift pitch Mp corresponds to width of a single transducer element, and transmission apertures Tx corresponding to two consecutive transmission events differ in position in the transducer element array direction by an amount corresponding to the width of a single transducer element. Note that the shift pitch Mp is not limited to the width of a single transducer element, and alternatively may correspond to width of one-half of a single transducer element. Further, the transmitter 1031 outputs information indicating the positions of transmission transducer elements composing the transmission aperture Tx to the data storage 107, via the control unit 108. For example, supposing that the probe 101 has 192 transducer elements 101a in total, the number of transmission transducer elements composing the transmission aperture Tx may be 20 to 100. Further, in the present disclosure, the term transmission event is used to refer to ultrasound transmission by the transmitter 1031, performed by using one transmission aperture (i.e., one set of transmission transducer elements of a predetermined number).

Figure 2:
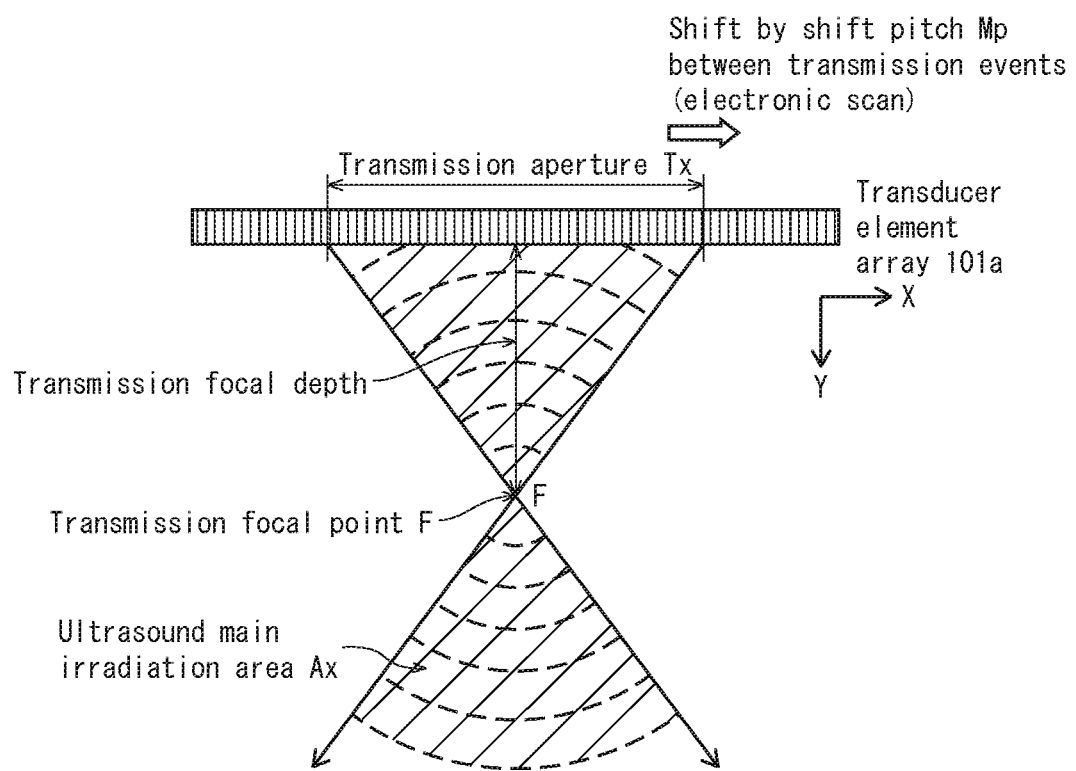
FIG. 2 is a schematic illustrating a propagation path of ultrasound beam transmitted from a transmission beam former 103 pertaining to the embodiment.

FIG. 2 is a schematic illustrating a propagation path of ultrasound transmitted by the transmission beam former 103. FIG. 2 illustrates a transmission aperture Tx for one transmission event (i.e., a transmission transducer element array composed of transmission transducer elements 101a that contribute to ultrasound transmission in the transmission event). Further, the transmission array direction length of the transmission aperture Tx is considered the length of the transmission aperture Tx.

The transmission beam former 103 controls ultrasound transmission by the transmission transducer elements such that a transmission transducer element closer to the center position of the transmission aperture Tx transmits ultrasound later in the transmission event. Due to this, the wavefront of ultrasound transmitted from the transmission transducer elements composing the transmission aperture Tx converges at one point at a certain focal depth (i.e., the transmission focal point F). Note that the depth of the transmission focal point F (i.e., focal depth) can be set as desired or required. Here, the focal depth indicates a depth at which the largest amount of transmitted ultrasound converges in the transducer element array direction (X direction in FIG. 2), in other words, a depth at which the width of ultrasound beams in the X direction is the narrowest. The focal point F is a center position of ultrasound beams in the X direction at the focal depth. Note that the focal depth is constant for transmission events of a single frame. In other words, no change occurs in a relative relationship between the transmission aperture Tx and the focal point F for transmission events of a single frame. After converging at the transmission focal point F, the wavefront of the transmitted ultrasound spreads out as before converging at the transmission focal point F. Thus, the transmitted ultrasound propagates through an hourglass-shaped area whose base is defined by the transmission aperture Tx and which is partitioned from other areas inside the subject by two straight lines intersecting at the transmission focal point F. More specifically, ultrasound transmitted from the transmission aperture Tx propagates in the following manner. As the transmitted ultrasound advances in a depth direction of the subject from the transmission aperture Tx, the width thereof (X direction in FIG. 2) gradually decreases until reaching the minimum width at the transmission focal point F. Then, as the transmitted ultrasound advances further in the depth direction from the transmission focal point F (Y direction in FIG. 2), the width thereof increases (i.e., the ultrasound spreads out). In the following, the hourglass-shaped area described above is referred to as an ultrasound main irradiation area Ax. Note that as already described above, the transmission of ultrasound may be performed so that the ultrasound main irradiation area Ax converges around a single transmission focal point F.

2. Receive Beam Former 104

Figure 3:
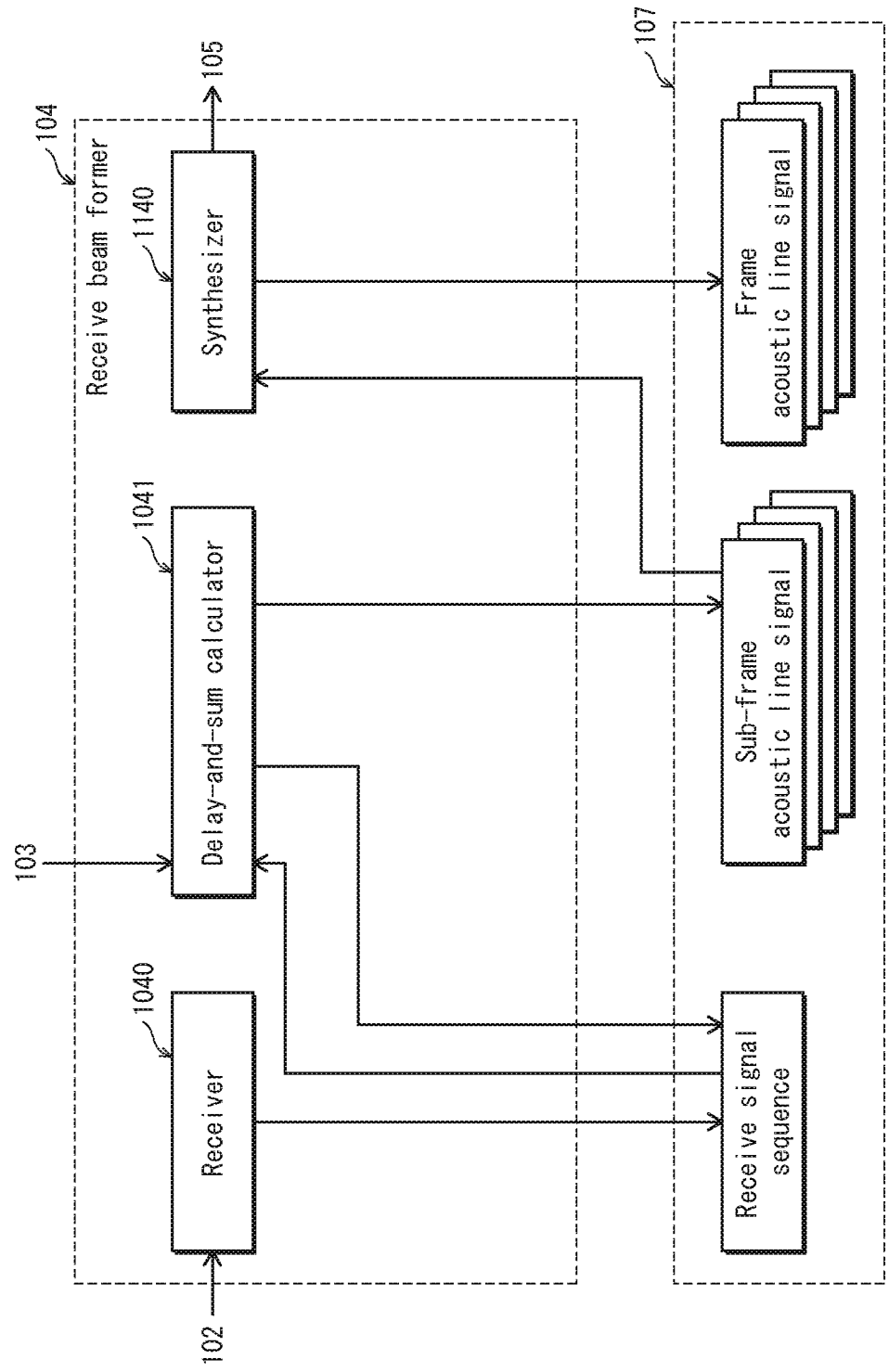
FIG. 3 is a functional block diagram illustrating the structure of a receive beam former 104 pertaining to the embodiment.

The receive beam former 104 generates acoustic line signals from electric signals acquired by a plurality of transducer elements 101a. The transducer elements 101a acquire the electric signals based on reflected ultrasound received by the probe 101. Here, an acoustic line signal for one measurement point is generated by performing delay-and-sum calculation with respect to receive signals from the measurement point. Description of the delay-and-sum calculation is provided later in the present disclosure. FIG. 3 is a functional block diagram illustrating the structure of the receive beam former 104. As illustrated in FIG. 3, the receive beam former 104 includes a receiver 1040, a delay-and-sum calculator 1041, and a synthesizer 1140.

The following describes the structure of each functional block of the receive beam former 104.

(1) Receiver 1040

The receiver 1040 is a circuit that is connected to the probe 101 via the multiplexer 102. For each transmission event, the receiver 1040 generates receive signals (RF signals). The receiver 1040 generates the receive signals by first receiving electric signals acquired through the probe 101 receiving reflected ultrasound, amplifying the received electric signals, and then performing A/D conversion on the amplified signals. For multiple transmission events, the receiver 1040 generates reception signals to output the reception signals to be stored in the data storage 107 one after another.

Here, the receiver 1040 generates one receive signal sequence (RF signal) for each of some or all of the transducer elements 101a. In specific, a receive signal sequence for a given transducer element is a digital signal yielded by performing amplification and A/D conversion on an electrical signal yielded through conversion of reflected ultrasound received by the transducer element, and is a sequence of signals along the ultrasound transmission direction (corresponding to the depth direction) that are received by the transducer element.

As discussed above, in each transmission event, the transmitter 1031 causes transmission transducer elements 101a composing the transmission aperture Tx, among the transducer elements 101a of the probe 101, each to transmit an ultrasound beam. Meanwhile, for each transmission event, the receiver 1040 receives electric signals converted in the probe 101 from reflected ultrasound acquired by each of some or all of the transducer elements 101a, thereby to generate a receive signal sequence for each of the transducer elements 101a from the received electric signals. In the present disclosure, the transducer elements 101a acquiring reflected ultrasound are referred to as receive transducer elements. Some or all of the receive transducer elements, namely receive transducer elements Rk, acquire reflected ultrasound from each of the measurement points. Here, it is preferable that the number of the receive transducer elements should be greater than the number of transmission transducer elements composing the transmission aperture Tx.

Then, the receiver 1040 stores the receive signal sequences to the data storage 107.

(2) Delay-and-Sum Calculator 1041

Figure 4:
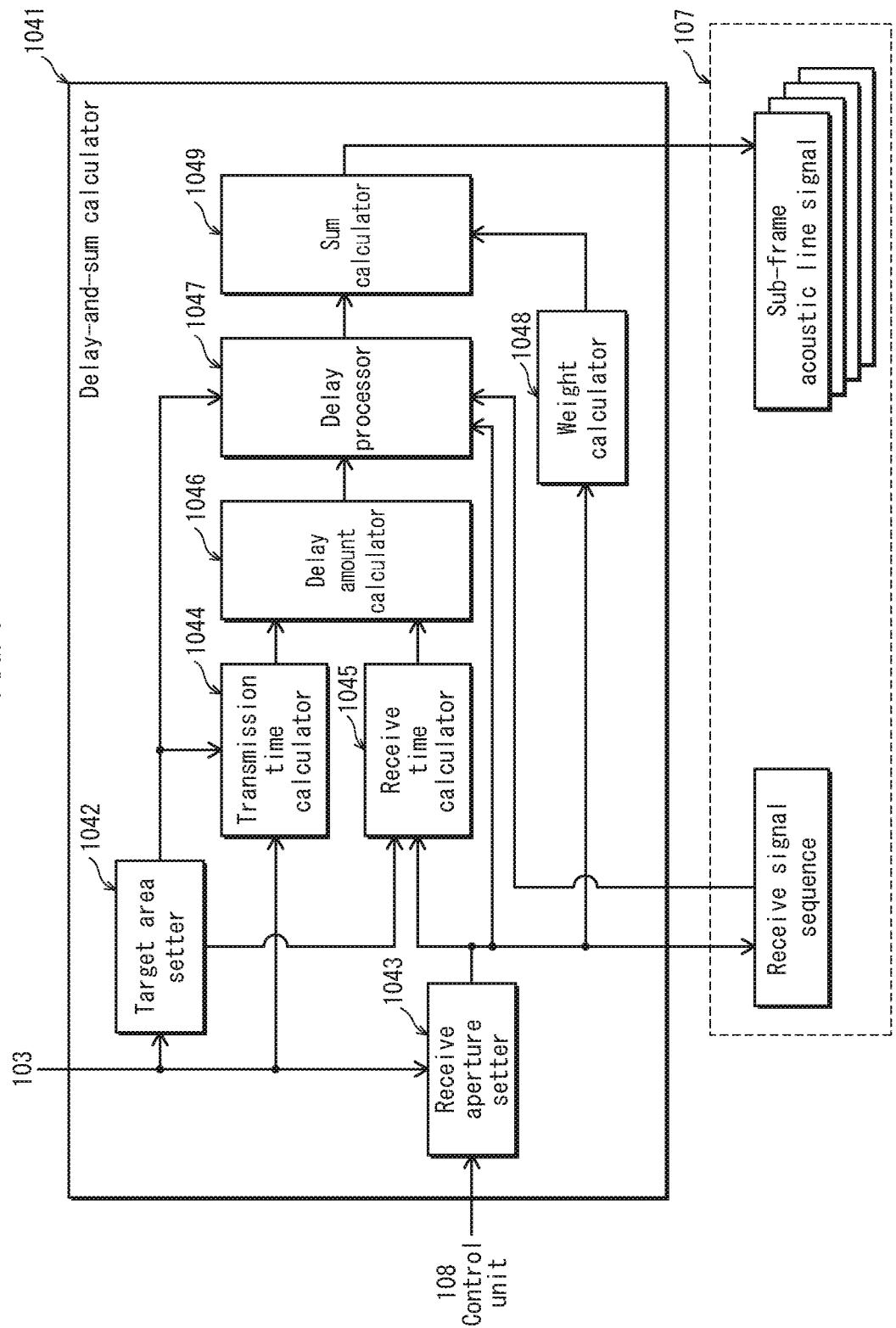
FIG. 4 is a functional block diagram illustrating the structure of a delay-and-sum calculator 1041 pertaining to the embodiment.

The delay-and-sum calculator 1041 is a circuit that sets a target area Bx for each transmission event. A target area Bx is an area in the subject from which one sub-frame acoustic line signal is to be generated. Further, the delay-and-sum calculator 1041 performs, for each measurement point Pij of the target area Bx, delay-and-sum calculation with respect to receive signal sequences corresponding to the measurement point Pij, each of which is received by one receive transducer element Rk. The delay-and-sum calculator 1041 performs this processing for each transmission event having been performed. The delay-and-sum calculator 1041 calculates an acoustic line signal for each of the measurement points Pij thereby to generate a sub-frame acoustic line signal. FIG. 4 is a functional block diagram illustrating the structure of the delay-and-sum calculator 1041. As illustrated in FIG. 4, the delay-and-sum calculator 1041 includes a target area setter 1042, a receive aperture setter 1043, a transmission time calculator 1044, a receive time calculator 1045, a delay amount calculator 1046, a delay processor 1047, a weight calculator 1048, and a sum calculator 1049.

The following describes the structure of each functional block of the delay-and-sum calculator 1041.

i) Target Area Setter 1042

The target area setter 1042 sets the target area Bx, which is an area in the subject from which one sub-frame acoustic line signal is to be generated. More specifically, in the present disclosure, the term "target area" is used to indicate a signal area for generating a sub-frame acoustic line signal for one transmission event. Further, one acoustic line signal is generated for each measurement point Pij of the target area Bx. In other words, the target area Bx is set for each transmission event in order to specify ones of the measurement points for which acoustic line signals are to be generated for the transmission event.

Further, in the present disclosure, a sub-frame acoustic line signal is a group of acoustic line signals that are generated from one transmission event. As already described above, from one transmission event, a plurality of acoustic line signals are generated, each for a different one of the measurement points Pij of the target area Bx. Further, a sub-frame is a unit corresponding to a group of signals which are acquired for one transmission event and each of which corresponds to a different one of the measurement points Pij of the target area Bx for the transmission event. Thus, a synthesizing result of multiple sub-frames acquired at different time points equals one frame.

For each transmission event, the target area setter 1042 sets the target area Bx based on the information indicating the position of the transmission aperture Tx for the transmission event, which is acquired from the transmission beam former 103.

Figure 5:
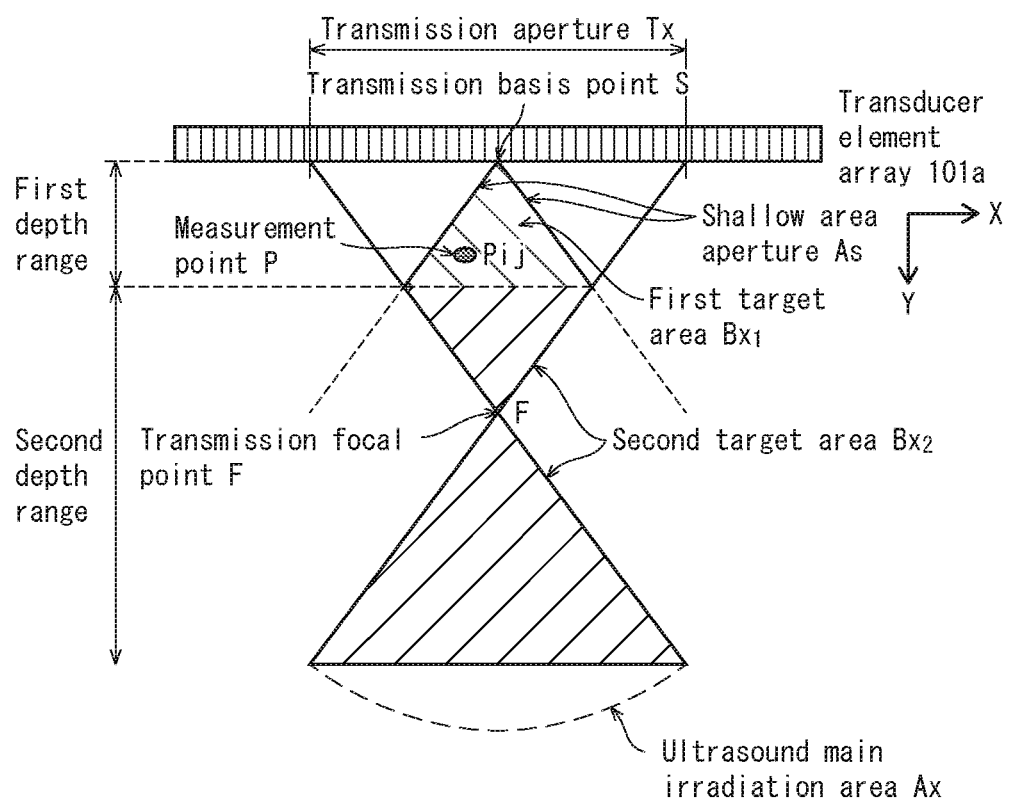
FIG. 5 is a schematic illustrating a target area Bx pertaining to the embodiment.

FIG. 5 is a schematic illustrating one example of the target area Bx. As illustrated in FIG. 5, the target area Bx is located in the ultrasound main irradiation area Ax, and includes a first target area $Bx_1$ located in a first depth range and a second target area $Bx_2$ located in a second depth range. The first depth range indicates a range from the shallowest depth to a predetermined depth. The second depth range indicates a range deeper than the predetermined depth. Also, the predetermined depth is shallower than the focal depth. The shallowest depth typically indicates a depth of a surface of a subject, the interface between the subject and the ultrasound probe, or a surface of the transducer element array, but is not limited to them. The predetermined depth is set for example such that a width of a shallow area aperture As described below in the transducer element array direction is equal to the width of the ultrasound main irradiation area Ax in the transducer element array direction. The second target area $Bx_2$ is all areas of the ultrasound main irradiation area Ax that are located in the second depth range. Meanwhile, the first target area $Bx_1$ is set such that the width in the transducer element array direction decreases as the depth decreases. More specifically, the first target area $Bx_1$ is an isosceles triangle whose vertex is located at the transmission basis point S, which is the center of the transmission aperture Tx. The first target area $Bx_1$ is an overlap area between the ultrasound main irradiation area Ax and the shallow area aperture As having a predetermined angle whose vertex is located at the transmission basis point S. The shape of the first target area $Bx_1$ is not limited to the above example, and alternatively may be any tapered shape so as to have the width in the transducer element array direction that decreases as the depth decrease. Also, the second target area $Bx_2$ may be part of the areas located in the second depth range in the ultrasound main irradiation area Ax. With this structure, it is possible to suppress the decrease in spatial resolution and S/N ratio due to the distance of the measurement point Pij located in the first depth range from the receive transducer element Rk. Also, it is possible to improve the use efficiency of ultrasound radiated on measurement points set in substantially all areas of the ultrasound main irradiation area Ax that are located in the second depth range, thereby to improve spatial resolution and S/N ratio by virtual transmission focusing.

The target area setter 1042 outputs the target area Bx to the receive aperture setter 1043, the transmission time calculator 1044, the receive time calculator 1045, and the delay processor 1047.

ii) Receive Aperture Setter 1043

The receive aperture setter 1043 is a circuit that sets, for each transmission event, a receive aperture Rx based on a control signal from the control unit 108 and information from the target area setter 1042 indicating the target area Bx. In specific, the receive aperture setter 1043 selects, for each measurement point Pij of the target Bx, some of the transducer elements 101a of the probe 101 as receive transducer elements forming a transducer element array (receive transducer element array) whose center position corresponds to a transducer element Xk spatially closest to the measurement point Pij. A receive transducer element Rk for each measurement point Pij is included in the receive aperture set for the measurement point Pij.

Figure 6:
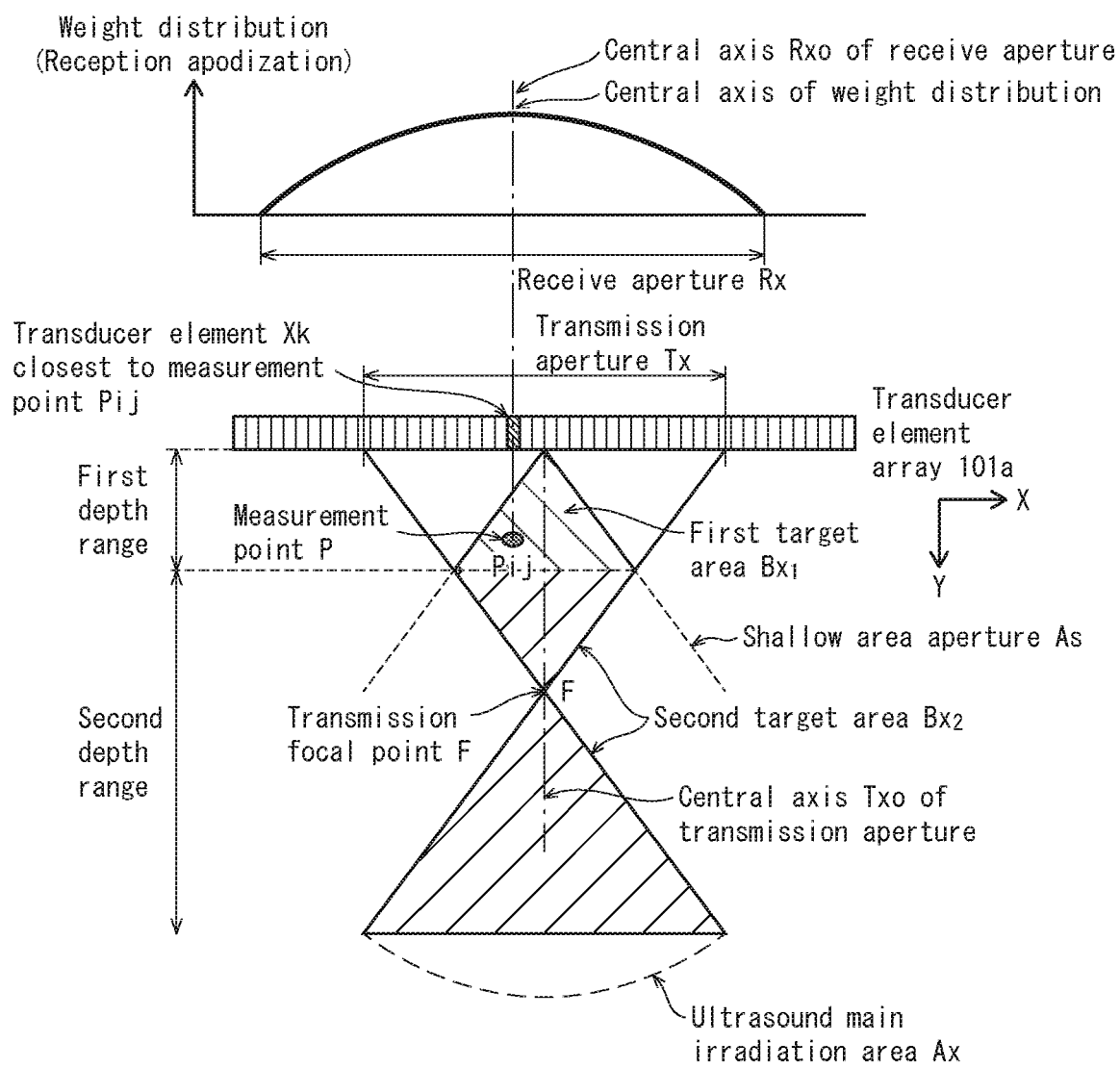
FIG. 6 is a schematic illustrating relationship between a transmission aperture Tx and a receive aperture Rx set by a receive aperture setter 1043 pertaining to the embodiment.

The receive aperture setter 1043 sets, for each measurement point Pij of the target area Bx for a transmission event, a receive aperture Rx (i.e., the receive transducer element array) so that the center position of the receive aperture Rx in the transducer element array direction corresponds to a transducer element Xk that is spatially closest to the measurement point Pij. FIG. 6 is a schematic illustrating the relationship between a transmission aperture Tx and a receive aperture Rx that the receive aperture setter 1043 sets. As illustrated in FIG. 6, for a given measurement point Pij, the receive aperture Rx is set so that the center position of the receive aperture Rx in the transducer element array direction corresponds to a transducer element Xk that is spatially closest to the measurement point Pij. Due to this, the position of the receive aperture Rx depends upon the position of the measurement point Pij, and does not change depending upon the position of the transmission aperture Tx, which shifts each time a transmission event is performed. That is, delay-and-sum calculation for generating an acoustic line signal for a given measurement point Pij is always performed based on receive signal sequences acquired by receive transducer elements Rk composing the same receive aperture Rx. This means that with respect to the measurement point Pij, the same receive aperture Rx is used in delay-and-sum calculation irrespective of transmission events.

The structure of the receive aperture setter 1043 is not limited to the above. The receive aperture setter 1043 may for example set a receive aperture Rx having the focal point F as its central axis. In order to utilize reflected ultrasound from the entirety of the ultrasound main irradiation area, the number of the receive transducer elements composing each receive aperture Rx is, beneficially, greater than or equal to the number of transmission transducer elements composing each transmission aperture Tx. The number of receive transducer elements composing the receive aperture Rx may be for example 32, 64, 96, 128, or 192.

The setting of the receive apertures Rx is performed at least by the number that is equal to the maximum number of measurement points Pij in the transducer element array direction. Further, the setting of receive apertures Rx may be performed each time a transmission event is performed as described above, or alternatively, receive apertures Rx for multiple transmission events having been performed may be set at once after the completion of the transmission events.

Further, the receive aperture setter 1043 outputs information indicating the positions of the receive transducer elements composing the receive aperture Rx to the data storage 107, via the control unit 108.

The data storage 107 outputs the information indicating the positions of the receive transducer elements composing the receive aperture Rx along with receive signal sequences for the receive transducer elements to each of the transmission time calculator 1044, the receive time calculator 1045, the delay processor 1047, and the weight calculator 1048.

iii) Transmission Time Calculator 1044

The transmission time calculator 1044 is a circuit that, for each transmission event, calculates a transmission time for each measurement point P of the target area Bx for the transmission event. The transmission time for a given measurement point P is the time amount required for transmitted ultrasound to arrive at the measurement point P. The transmission time calculator 1044 acquires information indicating the positions of the transmission transducer elements for a given transmission event from the data storage 107, and information indicating the position of the target area Bx for the transmission event from the target area setter 1042. Based on such information, the transmission time calculator 1044 calculates, for each measurement point Pij located in the target area Bx, the transmission time required for transmitted ultrasound to arrive at the measurement point Pij.

Figure 7A:
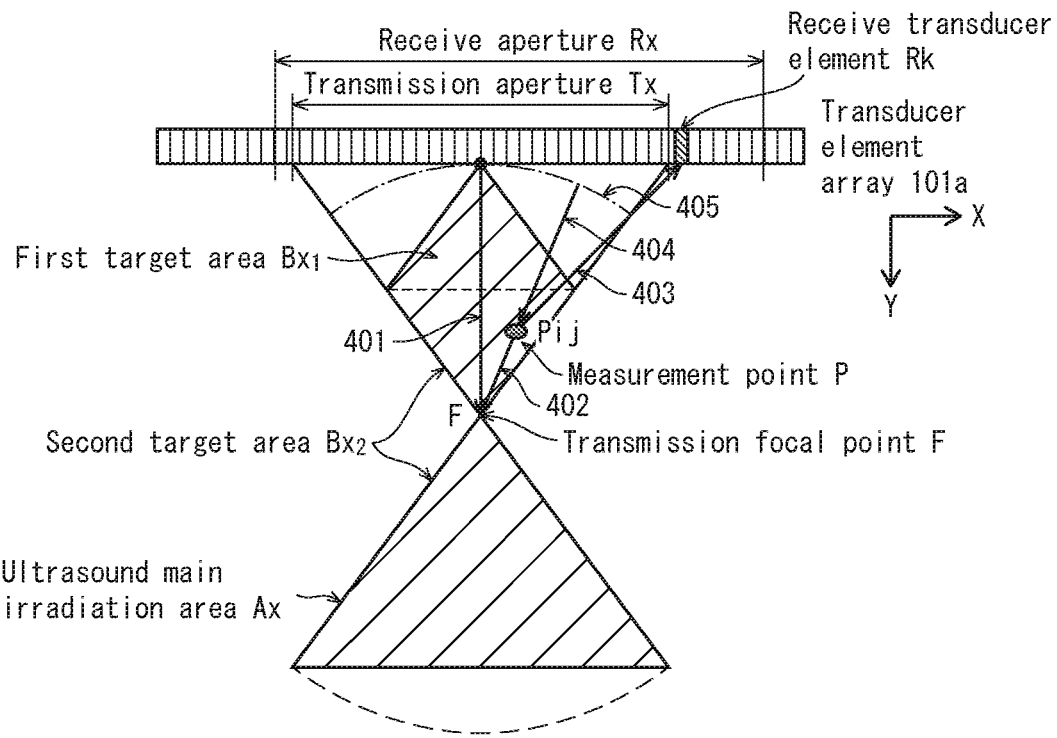
FIGS. 7A and 7B are schematics pertaining to the embodiment, each illustrating a propagation path of ultrasound that is transmitted from the transmission aperture Tx and arrives at a receive transducer element Rk via a measurement point Pij.
Figure 7B:
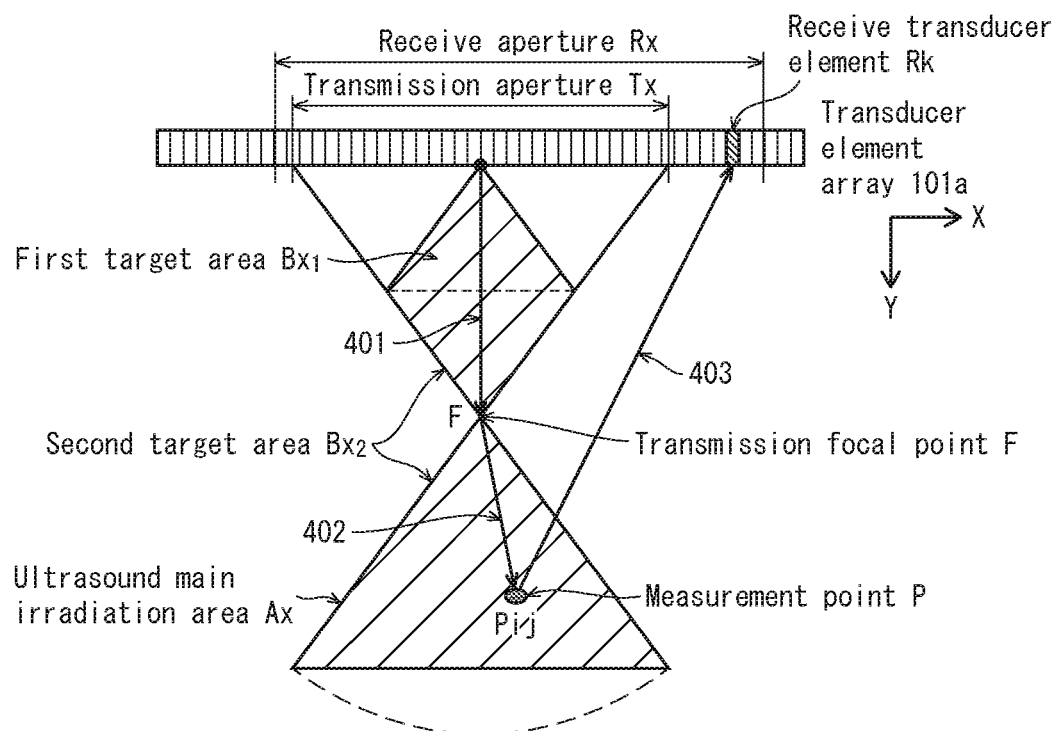

Each of FIGS. 7A and 7B is a schematic illustrating a propagation path of ultrasound that is transmitted from the transmission aperture Tx for a transmission event, is then reflected at a measurement point Pij of the target area Bx for the transmission event, and finally arrives at a receive transducer element Rk of the receive aperture Rx. Specifically, FIG. 7A illustrates the propagation path of ultrasound for a measurement point Pij located at or shallower than the focal depth. Meanwhile, FIG. 7B illustrates the propagation path of ultrasound for a measurement point Pij located deeper than the focal depth.

Following emission of ultrasound from the transmission aperture Tx, the wavefront of ultrasound converges at the transmission focal point F after travelling along the path 401. Subsequently, the wavefront spreads out once again and arrives at the measurement point Pij. When there is a change in acoustic impedance at the measurement point Pij, transmitted ultrasound generates reflected ultrasound, which is received by the receive transducer elements Rk of the receive aperture Rx. The transmission focal point F is stored in the device in advance upon designing of the transmission beam former 103. Thus, the length of the path 402 from the transmission focal point F to the measurement point Pij can be calculated geometrically.

The following describes how the transmission time is calculated in further detail.

First, the calculation of a transmission time for a measurement point Pij located at or shallower than the focal depth is described, with reference to FIG. 7A. Here, the time amount required for wavefront 405 of ultrasound transmitted from the transmission aperture Tx to arrive at the transmission focal point F by travelling along path 401 equals the time amount required for the wavefront 405 to travel along path 404 to arrive at the measurement point Pij and then travel along path 402 to arrive at the transmission focal point F from the measurement point Pij. As such, the transmission time for such a measurement point Pij is calculated by subtracting the time amount required for transmitted ultrasound to travel along the path 402 from the time amount required for transmitted ultrasound to travel along the path 401. Specifically, the transmission time for such a measurement point Pij can be calculated, for example, by dividing the length difference between the paths 401 and 402 by the velocity at which ultrasound propagates within the subject.

In the meantime, the following describes the calculation of a transmission time for a measurement point Pij located deeper than the transmission focal depth, with reference to FIG. 7B. Here, the transmission time for the measurement point Pij is calculated assuming that ultrasound transmitted from the transmission aperture Tx arrives at the transmission focal point F by travelling along path 401 and then travels along path 402 to arrive at the measurement point Pij from the transmission focal point F. As such, the transmission time for such a measurement point Pij is the total of the time amount required for transmitted ultrasound to travel along path 401 and the time amount required for transmitted ultrasound to travel along path 402. Specifically, the transmission time for such a measurement point Pij can be calculated, for example, by dividing the total of the lengths of paths 401 and 402 by the velocity at which ultrasound propagates within the subject.

Note that in the present embodiment, a transmission time for a measurement point Pij being located on the focal point is calculated by using a value obtained by subtracting the time amount required for transmitted ultrasound to travel along the path 402 from the time amount required for transmitted ultrasound to travel along the path 401. Alternatively, a transmission time for a measurement point Pij located on the focal point may be calculated by using the total of the time amount required for transmitted ultrasound to travel along path 401 and the time amount required for transmitted ultrasound to travel along path 402. This is because the length of the path 402 is zero in this case, and thus the transmission time for a measurement point Pij located on the focal point equals the time amount required for transmitted ultrasound to travel along path 401 with either calculation method.

For each transmission event, the transmission time calculator 1044 calculates the transmission time for each measurement point Pij of the target area Bx. That is, the transmission time calculator 1044 calculates, for each measurement point Pij, the time amount required for transmitted ultrasound to arrive at the measurement point Pij. Further, the transmission time calculator 1044 outputs the transmission time so calculated to the delay amount calculator 1046.

iv) Receive Time Calculator 1045

The receive time calculator 1045 is a circuit that calculates, for each measurement point P, a receive time required for reflected ultrasound from the measurement point P to arrive at each receive transducer element Rk of the receive aperture Rx. For a given transmission event, the receive time calculator 1045 acquires information indicating the positions of the receive transducer elements Rk for the given transmission event from the data storage 107, and acquires the information indicating the position of the target area Bx for the given transmission event from the target area setter 1042. Based on such information, the receive time calculator 1045 calculates, for each measurement point Pij of the target area Bx, the receive time required for transmitted ultrasound to arrive at each receive transducer element Rk after being reflected at the measurement point Pij.

As already discussed above, transmitted ultrasound arriving at a measurement point Pij generates reflected ultrasound when there is a change in acoustic impedance at the measurement point Pij. The reflected ultrasound is then received by receive transducer elements Rk of the receive aperture Rx. As discussed above, the receive time calculator 1045 acquires information indicating the positions of the receive transducer elements Rk of the receive aperture Rx from the data storage 107. Accordingly, the receive time calculator 1045 is able to geometrically calculate the length of paths 403 leading from the measurement point Pij to the respective receive transducer elements Rk.

For each transmission event, the receive time calculator 1045 calculates the receive time for each measurement point Pij of the target area Bx for the transmission event. That is, the receive time calculator 1045 calculates, for each measurement point Pij, the time required for transmitted ultrasound to arrive at each receive transducer element Rk after being reflected at the measurement point Pij. Further, the receive time calculator 1045 outputs the receive time so calculated to the delay amount calculator 1046.

v) Delay Amount Calculator 1046

The delay amount calculator 1046 is a circuit that calculates, for each receive transducer element Rk, a total propagation time based on the transmission time and the receive time for the receive transducer element Rk, and further calculates, for each receive transducer element Rk, a delay amount to be applied to a receive signal sequence for the receive transducer element Rk. In specific, the delay amount calculator 1046 acquires, from the transmission time calculator 1044, the transmission time required for ultrasound waves to arrive at a measurement point Pij. Further, for each receive transducer element Rk, the delay amount calculator 1046 acquires, from the receive time calculator 1045, the receive time required for ultrasound to be reflected at the measurement point Pij and arrive at the receive transducer element Rk. Then, the delay amount calculator 1046, for each receive transducer Rk, calculates a total propagation time required for transmitted ultrasound to arrive at the measurement point Pij, be reflected at the measurement point Pij, and then arrive at the receive transducer element Rk. Further, based on the difference between total propagation times for the receive transducer elements Rk, the delay amount calculator 1046 calculates a delay amount for each receive transducer element Rk. For each measurement point P of the target area Bx, the delay amount calculator 1046 calculates, for each receive transducer element Rk, the delay amount to be applied to a receive signal sequence for the receive transducer element Rk, and outputs the delay amounts to the delay processor 1047.

vi) Delay Processor 1047

The delay processor 1047 is a circuit that specifies, for each receive transducer element Rk, a receive signal based on reflected ultrasound from a measurement point Pij. In specific, for each receive transducer element Rk, the delay processor 1047 specifies a receive signal corresponding to the delay amount for the receive transducer element Rk from the receive signal sequence for the receive transducer element Rk.

More specifically, for each transmission event, the delay processor 1047 acquires, for each receive transducer element Rk, information indicating the position of the receive transducer element Rk from the receive aperture setter 1043, the receive signal sequence for the receive transducer element Rk from the data storage 107, the information indicating the position of the target area Bx from the target area setter 1042, and the delay amount to be applied to the receive signal sequence of the receive transducer element Rk from the delay amount calculator 1046. Further, for each receive transducer element Rk, the delay processor 1047 specifies a receive signal based on reflected ultrasound from a measurement point Pij. In specific, the delay processor 1047 specifies, from the receive signal sequence for the receive transducer element Rk, a receive signal corresponding to a time point after subtraction of the delay amount for the receive transducer element Rk. The delay processor 1047 outputs the receive signal so specified to the sum calculator 1049.

vii) Weight Calculator 1048

The weight calculator 1048 is a circuit that calculates a weight sequence (reception apodization weight) for the receive transducer elements Rk, so that the maximum weight is set with respect to the receive transducer element located at the center of the receive aperture Rx in the transducer element array direction.

As illustrated in FIG. 6, the weight sequence is a numerical sequence of weight coefficients that are to be applied to receive signals for the receive transducer elements composing the receive aperture Rx. The weight sequence indicates weights that are distributed symmetrically with respect to a transducer element xk that is spatially closest to the measurement point Pij. As the shape of distribution of the weights indicated by the weight sequence, any shape is applicable, including but not limited to a hamming window, a harming window, and a rectangular window. The weight sequence is set so that the maximum weight is set with respect to the receive transducer element located at the center position of the receive aperture Rx in the transducer element array direction, and the central axis of the weight distribution corresponds to the central axis Rxo of the receive aperture Rx. The weight calculator 1048 receives an input of information indicating the positions of the receive transducer elements Rk, which is output from the receive aperture setter 1043, and calculates the weight sequence for the receive transducer elements Rk for output to the sum calculator 1049. In the above structure, the weight sequence indicates weights distributed symmetrically with respect to the transducer element xk, which is spatially closest to the measurement point Pij. Alternatively, the weight sequence may indicate weights distributed symmetrically with respect to the transmission focal point F.

viii) Sum Calculator 1049

The sum calculator 1049 is a circuit that generates a delayed-and-summed acoustic line signal for each measurement point Pij, by receiving an input of the specified receive signals for the receive transducer elements Rk, which are output from the delay processor 1047, and summing together the specified receive signals. Alternatively, the sum calculator 1049 may generate an acoustic line signal for each measurement point P by receiving an input of the weight numerical sequence for the receive transducer elements Rk, which is output from the weight calculator 1048, multiplying the specified receive signal for each receive transducer element Rk with a corresponding weight, and summing the weighted receive signals. The sum calculator 1049 sums the receive signals for the receive transducer elements Rk, after the receive signals have been put in the same phase by the delay processor 1047. Due to this, the sum calculator 1049 is capable of increasing the S/N ratio of the receive signals received by the receive transducer elements Rk based on reflected ultrasound from the measurement point Pij, and receive signals for the measurement point Pij can be extracted.

As a result of one transmission event and processing accompanying the transmission event, an acoustic line signal is generated for each measurement point Pij of the target area Bx. Further, by repetitively performing transmission events while shifting the transmission aperture Tx in the transducer element array direction by the shift pitch Mp each time, all of the transducer elements 101a in the probe 101 perform ultrasound transmission. Then, a sub-frame acoustic line signal is generated for each transmission event, and sub-frame acoustic line signals for multiple transmission events are synthesized. As a result, a frame acoustic line signal, which is a synthesizing result of acoustic line signals corresponding to one frame, is generated.

In the present embodiment, acoustic line signals for respective measurement points, which compose the frame acoustic line signal and each of which is generated by synthesizing a plurality of acoustic line signals corresponding to the measurement point that are included in different sub-frame acoustic line signals, are each referred to as a synthesized acoustic line signal for the measurement point.

The sum calculator 1049, for each transmission event, generates a sub-frame acoustic line signal being a synthesizing result of acoustic line signals for every measurement point Pij of the target area Bx for the transmission event. Further, the sum calculator 1049 outputs the sub-frame acoustic line signals so generated to be stored in the data storage 107.

(5) Synthesizer 1140

Figure 8:
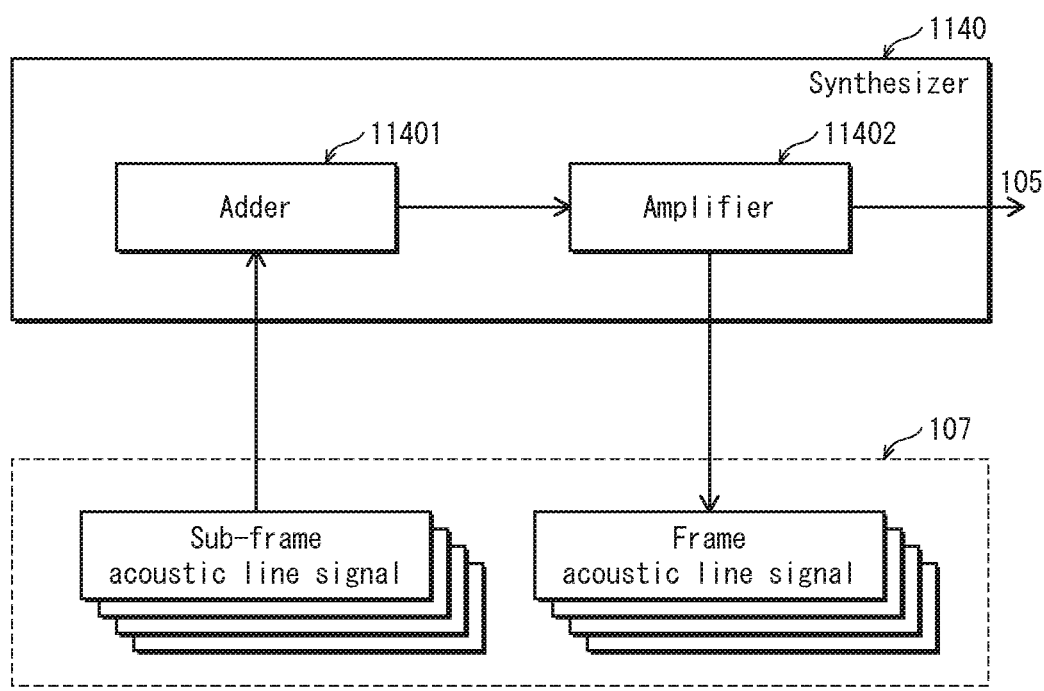
FIG. 8 is a functional block diagram illustrating the structure of a synthesizer 1140 pertaining to the embodiment.

The synthesizer 1140 is a circuit that generates a frame acoustic line signal by synthesizing a plurality of sub-frame acoustic line signals each generated for one transmission event. FIG. 8 is a functional block diagram illustrating the structure of the synthesizer 1140. As illustrated in FIG. 8, the synthesizer 1140 includes an adder 11401 and an amplifier 11402. As illustrated in FIG. 8, the synthesizer 1140 includes an adder 11401 and an amplifier 11402.

The following describes the structure of each functional block of the synthesizer 1140.

i) Adder 11401

The adder 11401, after the generation of a series of sub-frame acoustic line signals necessary for generating one frame acoustic line signal is completed, reads out the sub-frame acoustic line signals from the data storage 107. Further, the adder 11401 generates a frame acoustic line signal by synthesizing the plurality of sub-frame acoustic line signals. The synthesizing of the sub-frame acoustic line signals is performed according to the positions of the measurement points Pij, such that in the process, a synthesized acoustic line signal is generated for each measurement point Pij. In specific, the adder 11401 generates a synthesized acoustic line signal for a given measurement point Pij by synthesizing a plurality of acoustic line signals corresponding to the measurement point Pij that are included in different sub-frame acoustic line signals. Due to this, acoustic line signals for the same measurement point that are included in different sub-frame acoustic line signals are synthesized, to generate a synthesized acoustic line signal for the measurement point.

Figure 9:
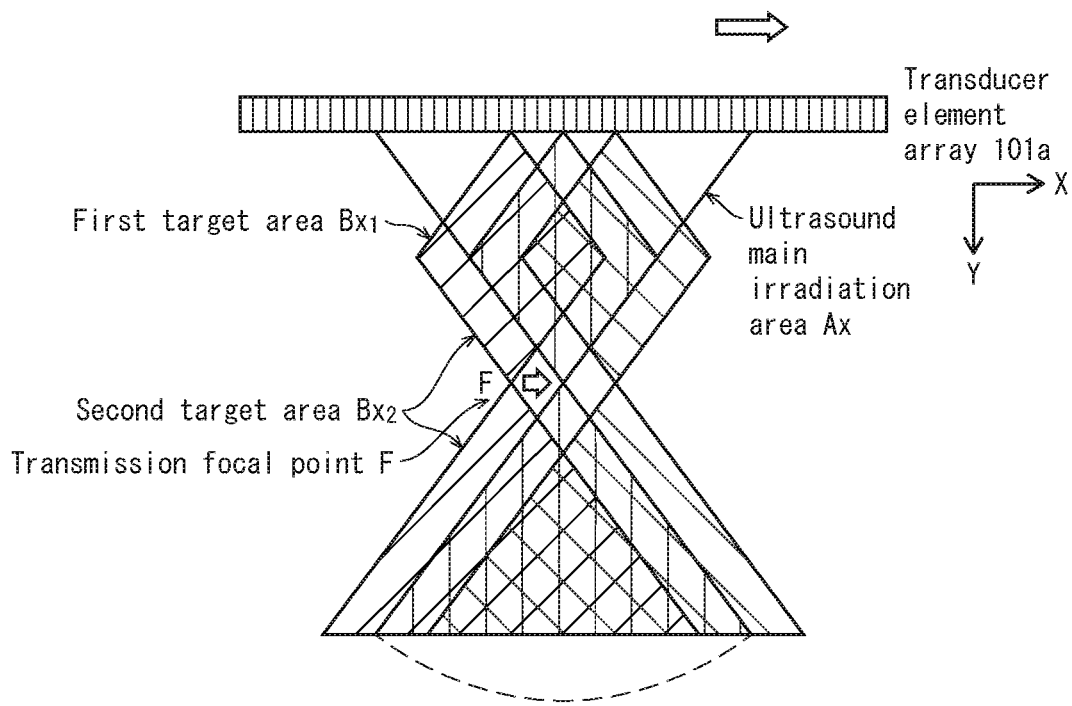
FIG. 9 is a schematic illustrating processing by an adder 11401 pertaining to the embodiment for generating a synthesized acoustic line signal.

FIG. 9 is a schematic illustrating processing by the adder 11401 for generating a synthesized acoustic line signal. As already discussed above, ultrasound transmission is performed by repetitively performing transmission events while shifting the transmission transducer element array (i.e., the transmission aperture Tx) in the transducer element array direction by width of a single transducer element each time. Due to this, target areas Bx for two consecutive transmission events differ in position from one another in the transducer element array direction by the width of the single transducer element. Thus, a frame acoustic line signal covering all target areas Bx can be generated by synthesizing sub-frame acoustic line signals based on the positions of the measurement points Pij from which the acoustic line signals included in the sub-frame acoustic line signals are acquired.

Further, for a measurement point included in multiple target areas Bx, values of a plurality of acoustic line signals included in different sub-frame acoustic line signals are summed. Thus, the synthesized acoustic line signal for such a measurement point may indicate a great value, depending upon the number of target areas Bx in which the measurement point is included. In the following, the number of different target areas Bx in which a given measurement point is included is referred to as an overlap count of the measurement point, and the maximum value of the overlap count in the transducer element array direction is referred to as a maximum overlap count.

Figure 10A:
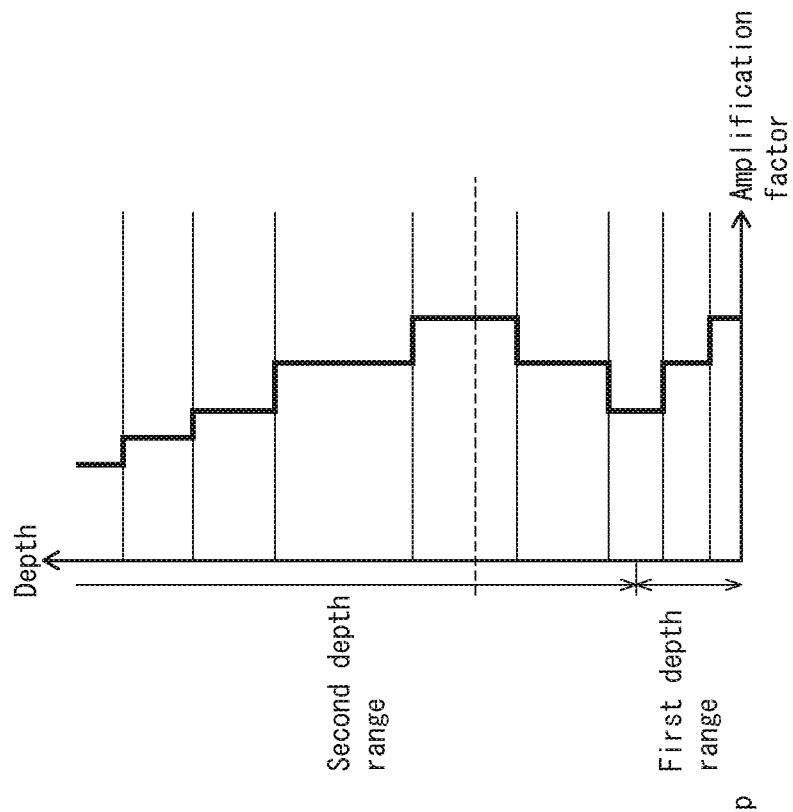
FIGS. 10A and 10B are schematics pertaining to the embodiment, providing an overview of maximum overlap counts of synthesized acoustic line signals and amplification by an amplifier 11402.

Further, in the present embodiment, the target area Bx has an hourglass-shape. As illustrated in FIG. 10A, the overlap count fluctuates in the depth direction of the subject. Accordingly, there is a depth-direction fluctuation in values of synthesized acoustic line signals due to the influence of the overlap count fluctuating in the depth direction. Note that, as described above, the first target area $Bx_1$ has the width in the transducer element array direction that decreases as the depth decreases. Accordingly, fluctuation of the overlap count relative to the depth in the first target area $Bx_1$ is similar to that in areas of the second target area $Bx_2$ that are located deeper than the focal depth.

Note that in synthesizing sub-frame acoustic line signals based on the positions of the measurement points Pij from which the acoustic line signals included in the sub-frame acoustic line signals are acquired to generate synthesized acoustic line signals for the respective measurement points, the adder 11401 may add weights in accordance with the positions of the measurement points Pij.

The adder 11401 outputs the frame acoustic line signal so generated to the amplifier 11402.

ii) Amplifier 11402

As already described above, there is a depth-direction fluctuation in values of synthesized acoustic line signals due to the influence of the overlap count. In order to moderate such fluctuation in values of different synthesized acoustic line signals, the amplifier 11402, in synthesizing the synthesized acoustic line signals to generate the frame acoustic line signal, performs amplification of multiplying the synthesized acoustic line signals by amplification factors. Here, the amplifier 11402 determines an amplification factor for a given synthesized acoustic line signal according to the number of acoustic line signals synthesized to yield the synthesized acoustic line signal (the overlap count).

Figure 10B:
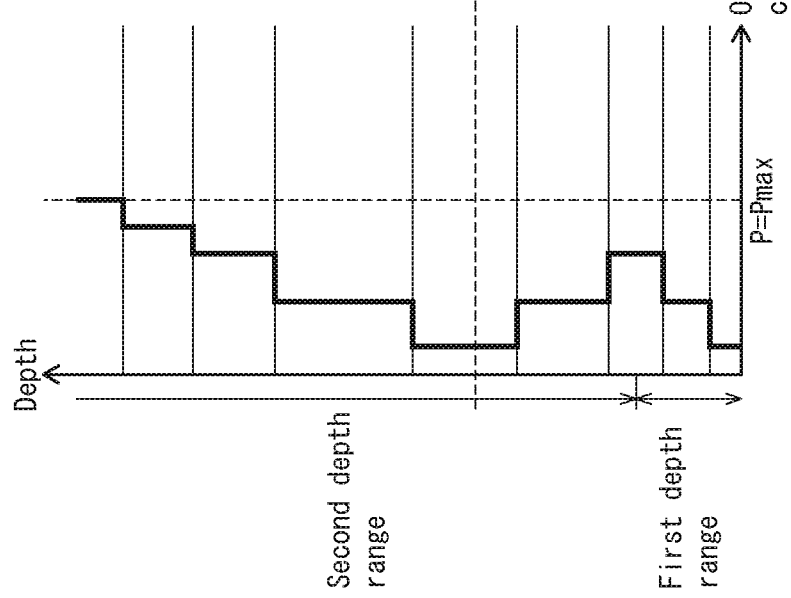

FIG. 10B is a schematic providing an overview of the amplification performed by the amplifier 11402. The maximum overlap count fluctuates in the depth direction of the subject, as illustrated in FIG. 10B. Thus, to compensate with this fluctuation in maximum overlap count, the amplifier 11402 multiplies the synthesized acoustic line signals by respective amplification factors that are based on the maximum overlap counts and vary in the depth direction, as illustrated in FIG. 10B. This moderates a difference between values of synthesized acoustic line signals deriving from the fluctuation in overlap counts in the depth direction, and thus the values of the synthesized acoustic line signals after the amplification are averaged out in the depth direction. That is, the amplification performed by the amplifier 11402 is gain equalization in the depth direction.

Further, the amplifier 11402 may also multiply the synthesized acoustic line signals by amplification factors varying in the transducer element array direction that are calculated based on overlap counts, when overlap counts fluctuate in the transducer element array direction. This moderates a difference between values of synthesized acoustic line signals deriving from the fluctuation in overlap counts in the transducer element array direction, and thus the values of the synthesized acoustic line signals after the amplification are averaged out in the transducer element array direction.

Here, note that the amplifier 11402 may generate the frame acoustic line signal by synthesizing amplified synthesized acoustic line signals for respective measurement points.

<Operations>

The following describes the operations of the ultrasound diagnostic device 100 having the structure described up to this point.

Figure 11:
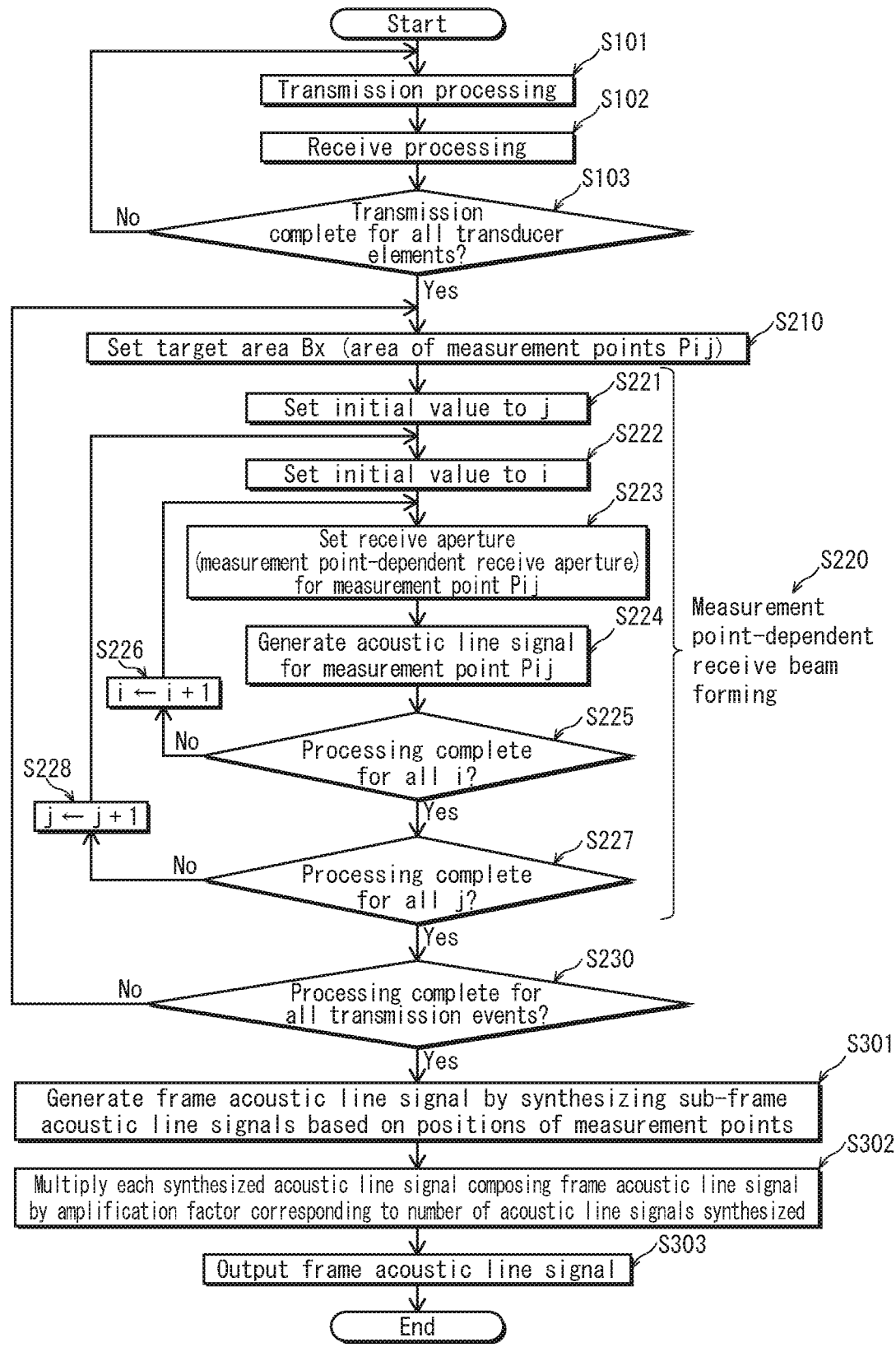
FIG. 11 is a flowchart illustrating operations of the ultrasound diagnostic device 100 pertaining to the embodiment for generating a frame acoustic line signal.

FIG. 11 is a flowchart illustrating operations of the ultrasound diagnostic device 100 for generating a frame acoustic line signal.

First, in Step S101, the transmitter 1031 performs transmission processing (a transmission event) of supplying a transmission signal causing transmission of an ultrasound beam to each transmission transducer element of the transmission aperture Tx.

In Step S102, the receiver 1040 generates receive signal sequences based on electric signals yielded through the reception of reflected ultrasound by the probe 101, and outputs the receive signal sequences to be stored in the data storage 107. Then, a determination is made of whether or not all transducer elements 101a of the probe 101 have performed ultrasound transmission (Step S103). When one or more of the transducer elements 101a have not yet performed ultrasound transmission, processing returns to Step S101, which results in another transmission event being executed by shifting the transmission aperture Tx in the transducer element array direction by the shift pitch Mp. Meanwhile, when all of the transducer elements 101a have performed ultrasound transmission, processing proceeds to Step S210.

In Step S210, the target area setter 1042 sets a target area Bx for a processing-target transmission event based on information indicating the position of the transmission aperture Tx for the processing-target transmission event. In the initial loop of processing, the target area setter 1042 sets a target area Bx for the initial transmission event, which can be calculated from the transmission aperture Tx for the initial transmission event.

Subsequently, processing proceeds to measurement-point dependent beam forming (Step S220 (including Steps S221 through S228)). In Step S220, first, coordinate values i and j indicating a position of a measurement point Pij of the target area Bx for the processing-target transmission event are initialized (set to the respective minimum possible values in the target area Bx) (Steps S221 and S222). Then, the receive aperture setter 1043 sets a receive aperture Rx for the current measurement point so that the center of the receive aperture Rx corresponds to a transducer element Xk that is spatially closest to the current measurement point Pij (Step S223).

Subsequently, an acoustic line signal is generated for the current measurement point Pij (Step S224).

Figure 12:
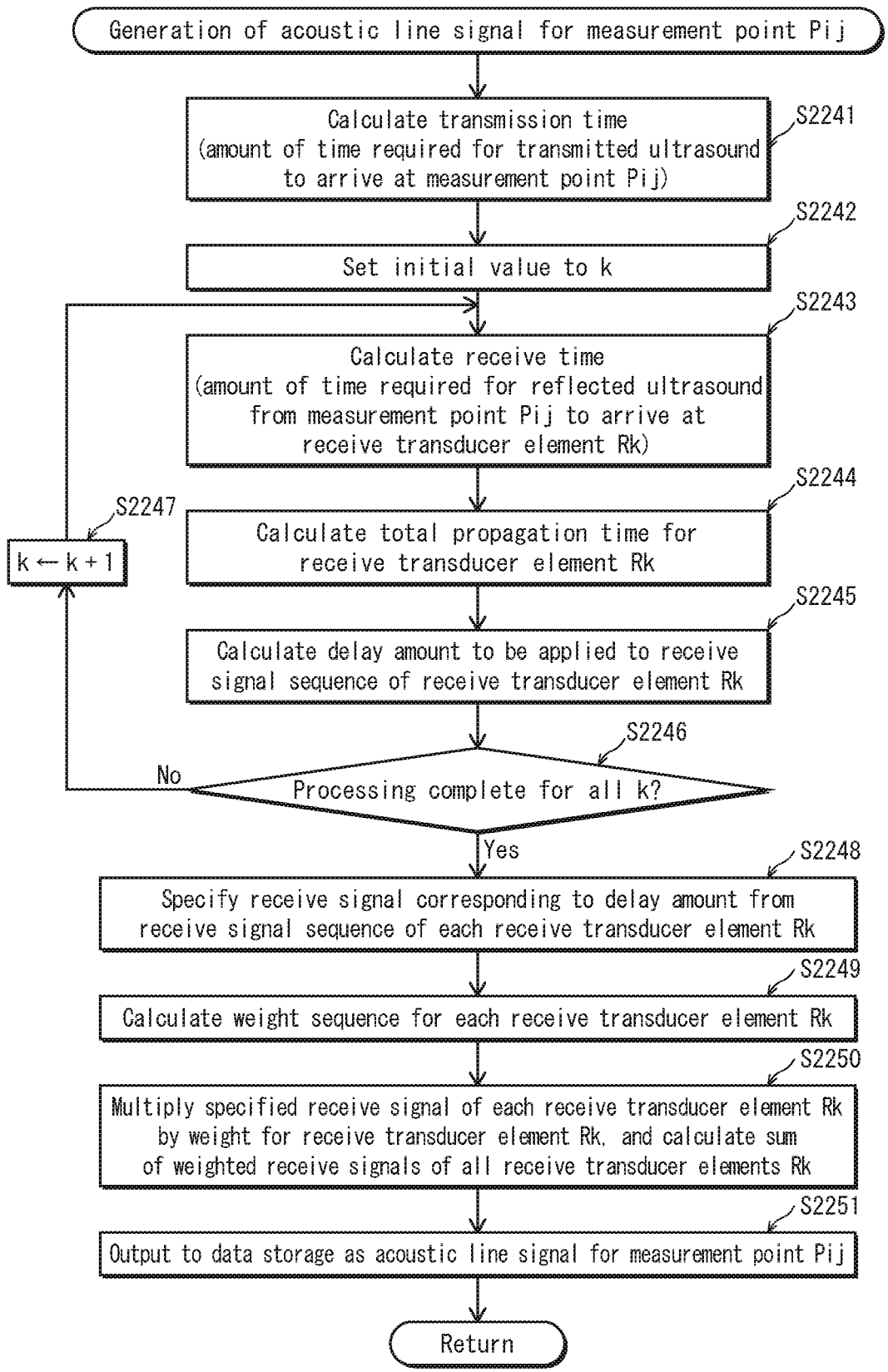
FIG. 12 is a flowchart illustrating operations of the receive beam former 104 pertaining to the embodiment for generating an acoustic line signal for a measurement point Pij.
Figure 13:
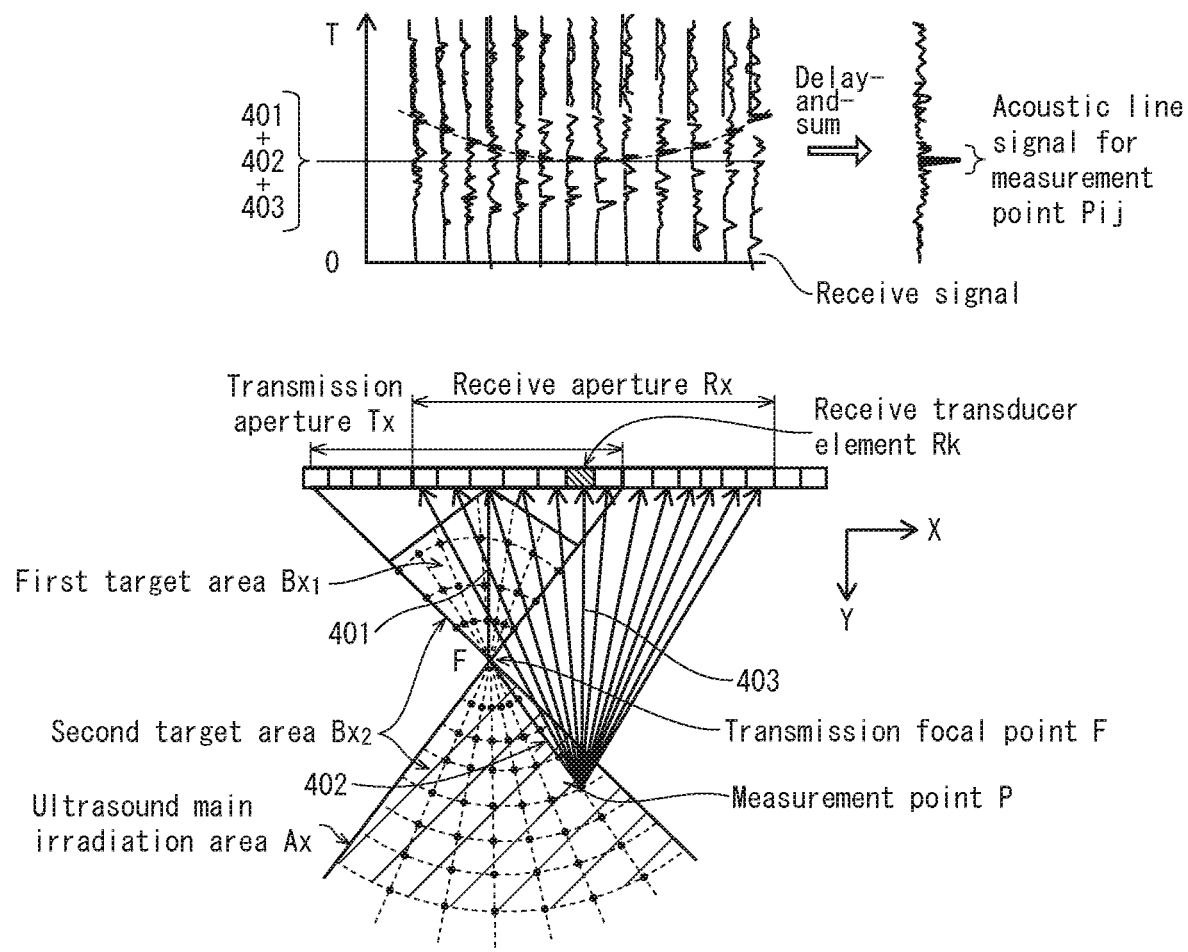
FIG. 13 is a schematic for explaining the operations of the receive beam former 104 pertaining to the embodiment for generating an acoustic line signal for a measurement point Pij.

The following describes the operations in Step S224 for generating an acoustic line signal for the current measurement point Pij. FIG. 12 is a flowchart illustrating the operations of the receive beam former 104 for generating the acoustic line signal for the current measurement point Pij. FIG. 13 is a schematic for explaining the operations of the receive beam former 104 for generating the acoustic line signal for the current measurement point Pij.

First, in Step S2241, the transmission time calculator 1044 calculates, for the current measurement point Pij, a transmission time required for transmitted ultrasound to arrive at the current measurement point Pij. As already described above, the current measurement point Pij is a measurement point of the target area Bx for the processing-target transmission event. Here, (i) when the current measurement point Pij is located deeper than the focal depth, the transmission time for the current measurement point Pij is calculated by dividing, by ultrasound velocity cs, the geometrically-calculable length of a path (combination of paths 401 and 402) starting at a transmission transducer element in the transmission aperture Tx and reaching the current measurement point Pij via the transmission focal point F. Meanwhile, (ii) when the current measurement point Pij is located at or shallower than the focal depth, the transmission time for the current measurement point is calculated by dividing, by the ultrasound velocity cs, a value (length of the path 401 minus length of the path 402) obtained by subtracting the geometrically-calculable length of the path from the transmission focal point F to the current measurement point Pij from the geometrically-calculable length of the path from a transmission transducer element in the transmission aperture Tx to the transmission focal point F.

Subsequently, value k, which indicates the position of a target receive transducer element Rk of the receive aperture Rx, is initialized (set to the minimum possible value in the receive aperture Rx) (Step S2242). Then, the receive time for the target receive transducer element Rk is calculated (Step S2243). The receive time is the time required for transmitted ultrasound to arrive at the target receive transducer element Rk after being reflected at the current measurement point Pij. The receive time for the target receive transducer element Rk can be calculated by dividing, by the ultrasound velocity cs, the geometrically-calculable length of the path 403 from the current measurement point Pij to the target receive transducer element Rk. Further, from a sum of the transmission time and the receive time for the target receive transducer element Rk, the total propagation time required for ultrasound transmitted from the transmission aperture Tx to arrive at the target receive transducer element Rk after being reflected at the current measurement point Pij is calculated (Step S2244). Further, based on the difference in total propagation time between different receive transducer elements Rk composing the receive aperture Rx, the delay amount for the target receive transducer element Rk is calculated (Step S2245).

Subsequently, a determination is performed of whether or not a delay amount has been calculated for every receive transducer element Rk composing the receive aperture Rx (Step S2246). When a delay amount has not yet been calculated for one or more of the receive transducer elements Rk, the value k is incremented (Step S2247), and a delay amount for another receive transducer element Rk is calculated (Step S2243). Meanwhile, when a delay amount has been calculated for every receive transducer element Rk composing the receive aperture Rx, processing proceeds to Step S2248. Note that at this point, a delay amount for the current measurement point Pij has already been calculated for each receive transducer element Rk of the receive aperture Rx. The delay amount for a given receive transducer element Rk indicates delay with which reflected ultrasound from the current measurement point Pij arrives at the receive transducer element Rk.

In Step S2248, the delay processor 1047, for each receive transducer element Rk, specifies a receive signal based on reflected ultrasound from the current measurement point Pij. Here, the delay processor 1047 specifies, from a receive signal sequence corresponding to each receive transducer element Rk, a receive signal corresponding to a time point after subtraction of the delay amount for the receive transducer element Rk.

Subsequently, the weight calculator 1048 calculates a weight sequence for the receive transducer elements Rk of the current receive aperture Rx, so that the maximum weight is set with respect to the receive transducer element located at the center position of the receive aperture Rx in the transducer element array direction (S2249). Then, the sum calculator 1049 generates an acoustic line signal for the current measurement point Pij by multiplying the specified receive signal for each receive transducer element Rk by a weight corresponding to the receive transducer element Rk, and summing the weighted receive signals for the different receive transducer elements Rk (Step S2250). Following this, the sum calculator 1049 outputs the acoustic line signal for the current measurement point Pij to the data storage 107 to be stored in the data storage 107 (Step S2251).

Referring to FIG. 11 once again, subsequently, an acoustic line signal is generated for each measurement point Pij (each illustrated in FIG. 13 as a black dot) of the target area Bx for the processing-target transmission event, by repeating Steps S223 and S224 while incrementing the coordinate values i and j (Steps S225 and S227). Subsequently, a determination is performed of whether or not an acoustic line signal has been generated for every measurement point Pij of the target area Bx. When an acoustic line signal has not yet been generated for every measurement point Pij of the target area Bx, the coordinate values i and j are incremented, yielding an acoustic line signal for another measurement point Pij (Step S224). Meanwhile, when an acoustic line signal has already been generated for every measurement point Pij of the target area Bx, processing proceeds to Step S230. At this point, an acoustic line signal has already been generated for each measurement point P of the target area Bx corresponding to the processing-target transmission event, and the acoustic line signals have been output to and stored to the data storage 107. In other words, a sub-frame acoustic line signal for the processing-target transmission event has been generated, and output to and stored to the data storage 107.

Subsequently, a determination is performed of whether or not a sub-frame acoustic line signal has been generated for each transmission event having been performed (Step S230). When sub-frame acoustic line signals have not yet been generated for one or more transmission events, processing proceeds to Step S210, where the coordinate values i and j are initialized (set to the respective minimum possible values in the target area Bx for the subsequent transmission event, which can be calculated from the transmission aperture Tx for the subsequent transmission event) (Steps S221 and S222), and then setting of a receive aperture Rx is performed (Step S223) and generation of acoustic line signals is performed (Step S224). Meanwhile, when sub-frame acoustic line signals have been generated for every transmission event having been performed, processing proceeds to Step S301.

In Step S301, the adder 11401 reads out the sub-frame acoustic line signals stored in the data storage 107, and synthesizes the sub-frame acoustic line signals based on positions of the measurement points Pij. Thus, a synthesized acoustic line signal is generated for each measurement point Pij, and accordingly a frame acoustic line signal is generated. Subsequently, the amplifier 11402 multiples each synthesized acoustic line signal by a corresponding amplification factor that is determined based on the number of acoustic line signals, included in the sub-frame acoustic line signals, that have been synthesized to yield the synthesized acoustic line signal (Step S302). Further, the amplifier 11402 outputs the amplified frame acoustic line signal to the ultrasound image generator 105 and the data storage 107 (Step S303), and processing is terminated.

<Determination Method of Shallow Area Aperture As>

The following describes in further detail a determination method of the shallow area aperture As defining the shape of the first target area Bx.

As described above, the first target area $Bx_1$ has the width in the transducer element array direction that decreases as the depth decreases. Due to this, it is preferable that the shallow area aperture As should be determined so as to have a predetermined angle whose vertex is located at the center of the transmission aperture Tx, and an overlap area between the shallow area aperture As and the ultrasound main irradiation area Ax should be determined as the first target area Bx.

(1) Reception Dynamic Aperture

Figure 15A:
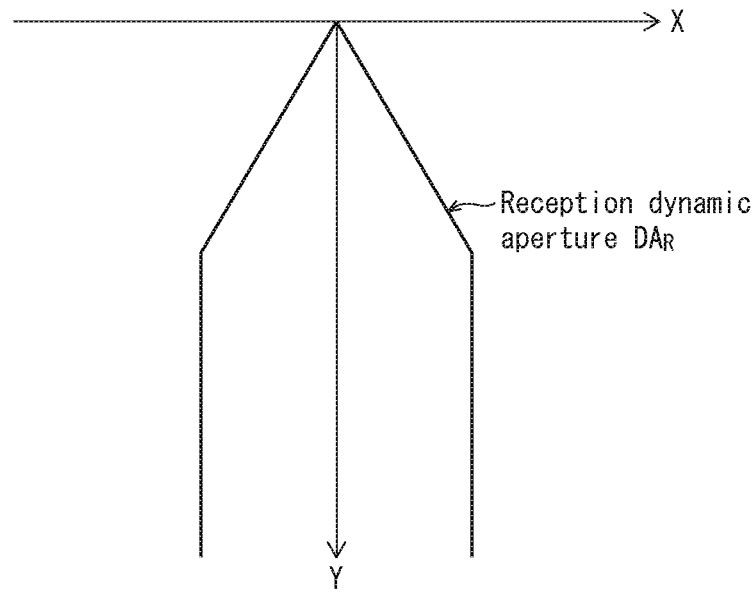
FIGS. 15A and 15B illustrate a first setting example of a shallow area aperture As pertaining to the embodiment.
Figure 15B:
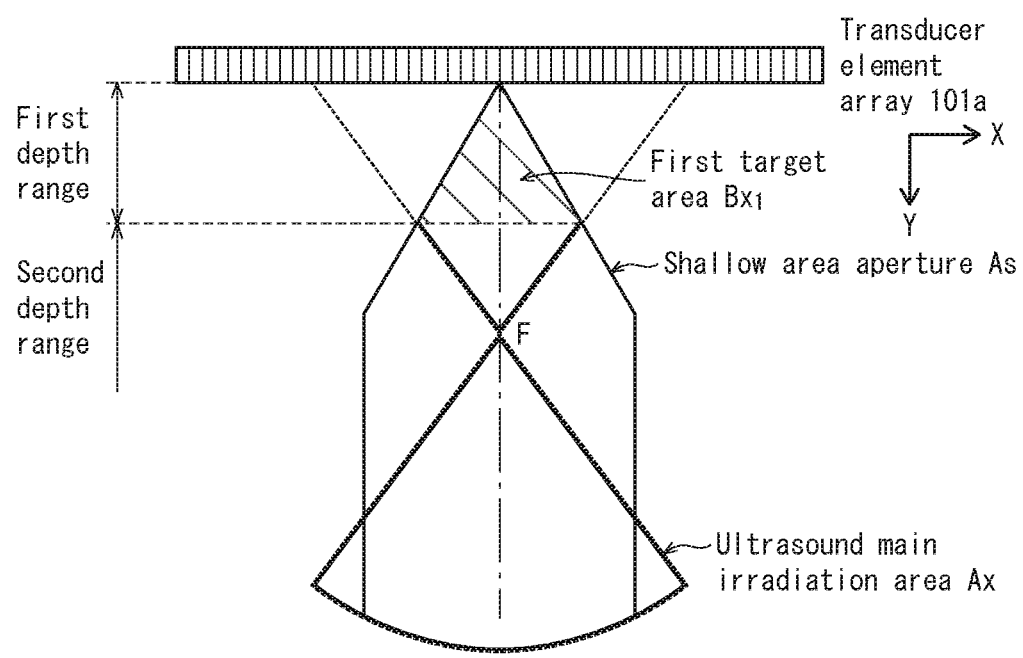

One example of the determination method of the shallow area aperture As is a method using a reception dynamic aperture. FIG. 15A is a schematic illustrating a reception dynamic aperture. As described above, as the depth at which the measurement point is located decreases, reception signals corresponding to receive transducer elements Rk distant from the measurement point exhibit lower S/N ratio. To respond to this, a proposal has been a method of setting a receive aperture having the center that coincides with a central axis Txo of a transmission aperture, such that, with respect to a measurement point located at or deeper than a predetermined depth, the width of the receive aperture in the transducer element array direction decreases towards shallower depths to satisfy a proportional relationship between the width of the receive aperture in the transducer element array direction and the depth of the measurement point. This receive aperture determination method is referred to as a reception dynamic aperture. In the present embodiment, this reception dynamic aperture is applied to virtual transmission focusing that utilizes the synthetic aperture method, and a reception dynamic aperture $DA_R$ is used as a shallow area aperture As without modification. As illustrated in the schematic in FIG. 15B, shallower depths and deeper depths than a depth at which the reception dynamic aperture $DA_R$ intersects the ultrasound main irradiation area Ax are respectively defined as a first depth range and a second depth range. In the first depth range, an overlap area between the ultrasound main irradiation area Ax and the shallow area aperture As is defined as a first target area $Bx_1$. This structure exhibits effects similar to those by the reception dynamic aperture in synthesizing sub-frame acoustic line signals to generate a frame acoustic line signal.

Note that the target area setter may hold therein in advance a parameter specifying shape of a reception dynamic aperture, and set a shallow area aperture As based on the parameter.

(2) Directional Characteristic of Transducer Elements

Figure 16A:
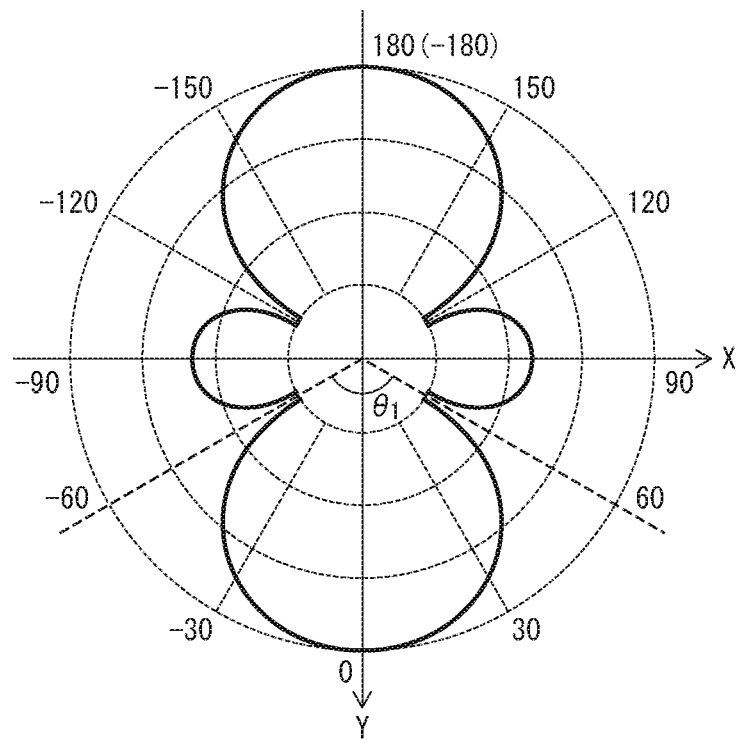
FIGS. 16A and 16B illustrate a second setting example of the shallow area aperture As pertaining to the embodiment.
Figure 16B:
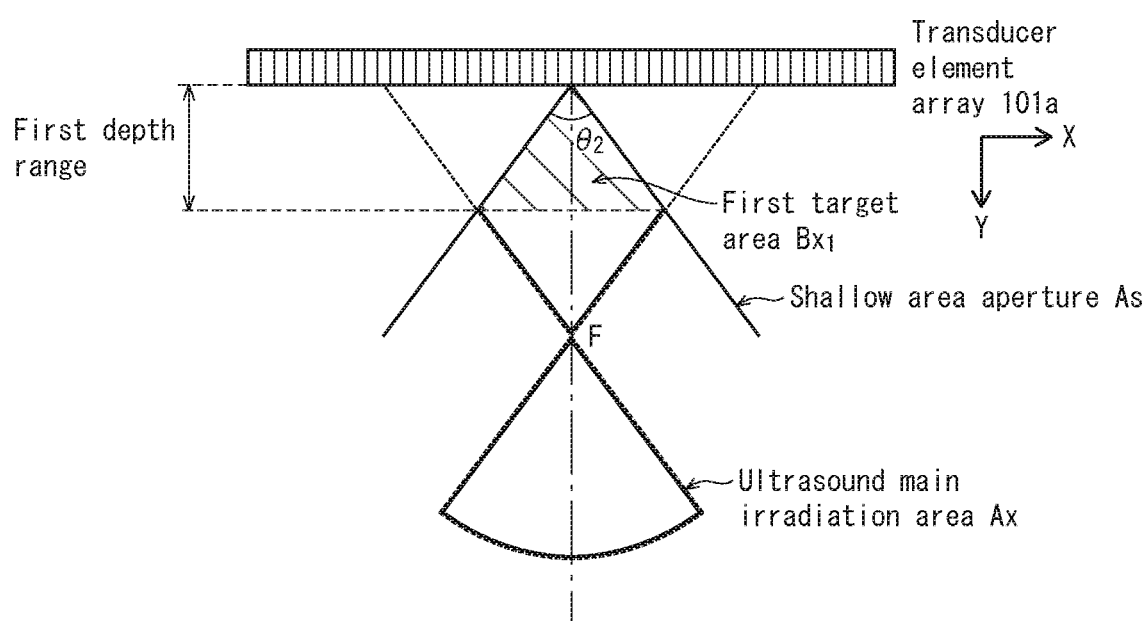

Another example of the determination method of the shallow area aperture As is a method using directional characteristic of the transducer elements 101a of the ultrasound probe 101. FIG. 16A is a schematic illustrating directional characteristic in terms of reception sensitivity of a single transducer element 101a at a predetermined frequency. As illustrated in FIG. 16A, the directional characteristic of the transducer element 101a is the maximum in the Y direction, and is the minimum in a direction at an angle of $\theta_1/2$ relative to the Y direction. Beams in this direction at the angle of $\theta_1/2$ relative to the Y direction are referred to also as null beams. In the present embodiment, a range where no null beam is included, that is, a range of the angle $\theta_2$ satisfying a relation $\theta_2 < \theta_1$ is defined as a shallow area aperture As. Then, as illustrated in the schematic in FIG. 16B, in the first depth range, an overlap area between the ultrasound main irradiation area Ax and the shallow area aperture As is defined as a first target area $Bx_1$. The shallow area aperture As may be set such that the directional characteristic in terms of reception sensitivity of the transducer element 101a includes a range equal to or higher than a predetermined standard. Note that the directional characteristic in terms of reception sensitivity of even the same transducer element 101a varies depending on ultrasound frequency. Thus, the target area setter should preferably change the shallow area aperture As according to frequency of ultrasound that is a transmission and reception target.

Note that the target area setter may hold therein in advance combinations of frequency of ultrasound that is a transmission and reception target, information indicating directional characteristic of transducer elements 101a, and a parameter defining a shallow area aperture As, and determine the shallow area aperture As based on the frequency of the target ultrasound, and the information indicating the directional characteristic of the transducer elements 101a.

(3) Reception Beam Profile

Figure 17A:
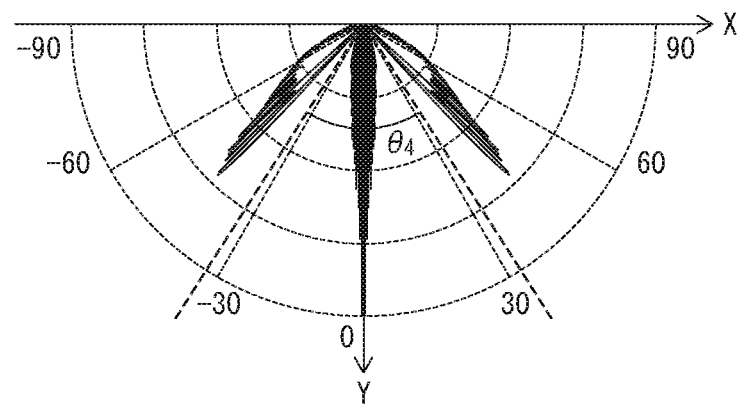
FIGS. 17A and 17B illustrate a third setting example of the shallow area aperture As pertaining to the embodiment.
Figure 17B:
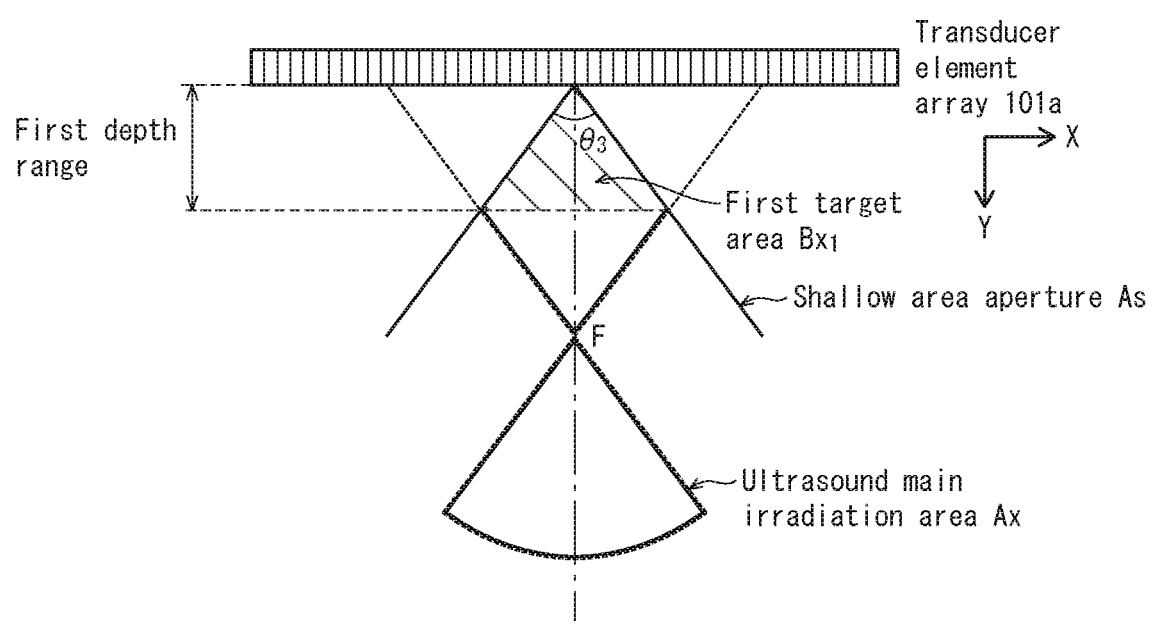

Further another example of the determination method of the shallow area aperture As is a method using a reception beam profile by directional characteristic of the ultrasound probe 101. FIG. 17A is a schematic illustrating directional characteristic in terms of reception sensitivity of the ultrasound probe 101 at a predetermined frequency. As illustrated in FIG. 17A, the directional characteristic in terms of reception sensitivity of the ultrasound probe 101 exhibits the maximum zero-order peak in the Y direction, and exhibits the primary peak called side lobe in a direction at a predetermined angle relative to the Y direction. In the present embodiment, a range of an angle $\theta_3$ satisfying a relation $\theta_3 < \theta_4$ is defined as a reception beam profile, where a range of the angle $\theta_4$ includes the zero-order peak and does not include the primary peak. Then, the range of the angle $\theta_3$ is defined as a shallow area aperture As. Note that the directional characteristic in terms of reception sensitivity of the ultrasound probe 101 varies depending on ultrasound frequency similarly to that of the transducer elements 101a. Thus, the target area setter may change the shallow area aperture As according to frequency of ultrasound that is a transmission and reception target.

Note that the target area setter may hold therein in advance combinations of frequency of ultrasound that is a transmission and reception target, information indicating directional characteristic of the ultrasound probe 101, and a parameter defining a shallow area aperture As, and determine the shallow area aperture As based on the frequency of the target ultrasound, and the information indicating the directional characteristic of the ultrasound probe 101.

<Summary of Embodiment 1>

As described above, the ultrasound diagnostic device 100 pertaining to the present embodiment, according to the synthetic aperture method, synthesizes acoustic line signals for the same measurement point P that are generated from different transmission events. This achieves the effect of performing virtual transmission focusing even for measurement points P that are located in depths other than that of the transmission focal point F. This improves spatial resolution and S/N ratio.

Also, the ultrasound diagnostic device 100 sets the second target area as the target area for which sub-frame acoustic line signals are to be generated, so that the second target area is all areas of the ultrasound main irradiation area that are located in the second depth range deeper than the predetermined depth. Accordingly, it is possible to improve the use efficiency of ultrasound and enjoy the effect of the synthetic aperture method of improving spatial resolution and S/N ratio to the maximum. Meanwhile, the ultrasound diagnostic device 100 sets, as the target area, the first target area in the first depth range which is shallower than the predetermined depth such that the width in the transducer element array direction that decreases as the depth decreases. Due to this, it is possible to suppress degradation of S/N ratio and spatial resolution with respect to measurement points located at shallow depths by not generating sub-frame acoustic line signals under conditions that the measurement points are distant from respective receive transducer elements Rk and S/N ratio is not sufficiently improved even by delay-and-sum calculation. Furthermore, by excluding the measurement points for which the S/N ratio is not sufficiently improved even by delay-and-sum calculation from the target area, it is possible to reduce delay-and-sum calculation amount while minimalizing the influence of degradation of frame acoustic line signal quality.

Further, in the ultrasound diagnostic device 100, the receive aperture setter 1043 selects, as transducer elements composing the receive aperture Rx for each measurement point P, transducer elements forming an array whose center position in the transducer element array direction matches a transducer element that is spatially closest to the measurement point P. Accordingly, the ultrasound diagnostic device 100 performs receive beam forming by using a receive aperture that is not dependent upon transmission events but is dependent upon the position of the measurement point P, and that is symmetric with respect to the measurement point P. Due to this, the receive aperture Rx for a given measurement point P does not change (i.e., the same receive aperture Rx is used for the same measurement point P) between different transmission events, between which the transmission focal point F is shifted in the transducer element array direction. Thus, delay-and-sum calculation for the same measurement point P is always performed by using the same receive aperture Rx. In addition, in the ultrasound diagnostic device 100, a weight sequence is set so that the closer a receive transducer element is to the measurement point P, the greater the weight applied to the receive transducer element. Due to this, even taking into account the fact that ultrasound decay increases as propagation distance increases, ultrasound reflected from the measurement point P can be used with the highest sensitivity. Accordingly, the ultrasound diagnostic device 100 achieves high spatial resolution and S/N ratio.

In the above embodiment, the receive aperture Rx for each measurement point P is selected so that center position of the receive aperture Rx in the transducer element array direction corresponds to a transducer element that is spatially closest to the measurement point P. Alternatively, the receive aperture Rx may be selected so that the center position of the receive aperture Rx corresponds to the focal point.

<Modification 1>

The receive aperture setter 1043 in the ultrasound diagnostic device 100 pertaining to the embodiment, for each measurement point P, the receive aperture Rx so that the center position of the receive aperture Rx in the transducer element array direction corresponds to a transducer element that is spatially closest to the measurement point P. Alternatively, the structure for selecting the receive aperture Rx may be changed as necessary, as long as acoustic line signals for all measurement points Pij of the target area Bx can be generated by calculating total propagation times and performing delaying based on total propagation paths. As already discussed above, a total propagation time for a given receive transducer element Rk is the time required for ultrasound transmitted from the transmission aperture Tx to reach the receive transducer element Rk after passing through the transmission focal point F and being reflected at the measurement point Pij.

Modification 1 provides an ultrasound diagnostic device differing from the ultrasound diagnostic device 100 pertaining to the embodiment for including a receive aperture setter (a Tx receive aperture setter) that sets, for each transmission event, the receive aperture Rx so that the center position of the receive aperture Rx corresponds to the center position of the transmission aperture Tx for the transmission event. That is, the receive aperture Rx in modification 1 can be referred to as a transmission-dependent receive aperture. Other than the Tx receive aperture setter, the components of the ultrasound diagnostic device pertaining to modification 1 have the same structures and configurations as the corresponding components in the ultrasound diagnostic device 100 described in the embodiment. Thus, description of such similar components is not provided in the following.

Figure 18:
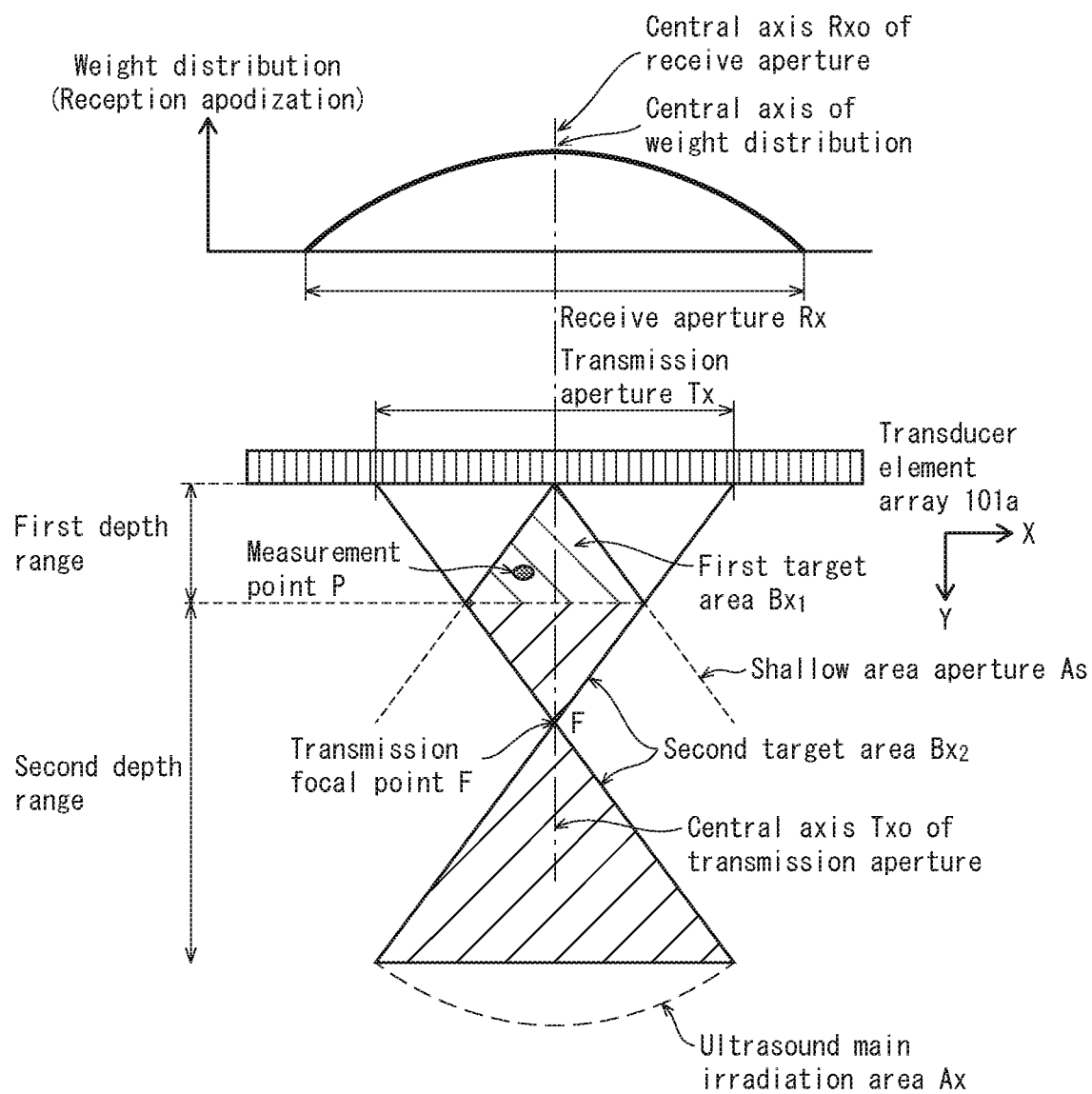
FIG. 18 is a schematic illustrating relationship between a transmission aperture Tx and a receive aperture Rx set by a Tx receive aperture setter pertaining to modification 1.

FIG. 18 is a schematic illustrating the relationship between a transmission aperture Tx and a receive aperture Rx set by the Tx receive aperture setter. In modification 1, the Tx receive aperture setter sets, for each transmission event, a receive aperture Rx so that the center position of the receive aperture Rx in the transmission element array direction corresponds to the center position of the transmission aperture Tx for the transmission event. Thus, the position of an axis Rxo passing through the center position of the receive aperture Rx corresponds to the position of an axis Txo passing through the center position of the transmission aperture Tx. Further, the receive aperture Rx is symmetric about the transmission focal point F (i.e., has the same number of apertures at both sides of the center position thereof in the transmission element array direction). As such, as the transmission aperture Tx shifts in the transducer element array direction from one transmission event to another, the receive aperture Rx also shifts in the transducer element array direction, following the transmission aperture Tx.

In addition, a weight sequence (so-called reception apodization weight) for the receive transducer elements Rk is calculated, so that the maximum weight is set with respect to a transducer element located along the central axis Rxo of the receive aperture Rx and the central axis Txo of the transmission aperture Tx. The weight sequence indicates weights distributed symmetrically with respect to the transducer element located along the central axis Rxo and the central axis Txo. As the shape of distribution of the weights indicated by the weight sequence, any shape is applicable, including but not limited to a hamming window, a hanning window, and a rectangular window.

<Operations>

Figure 19:
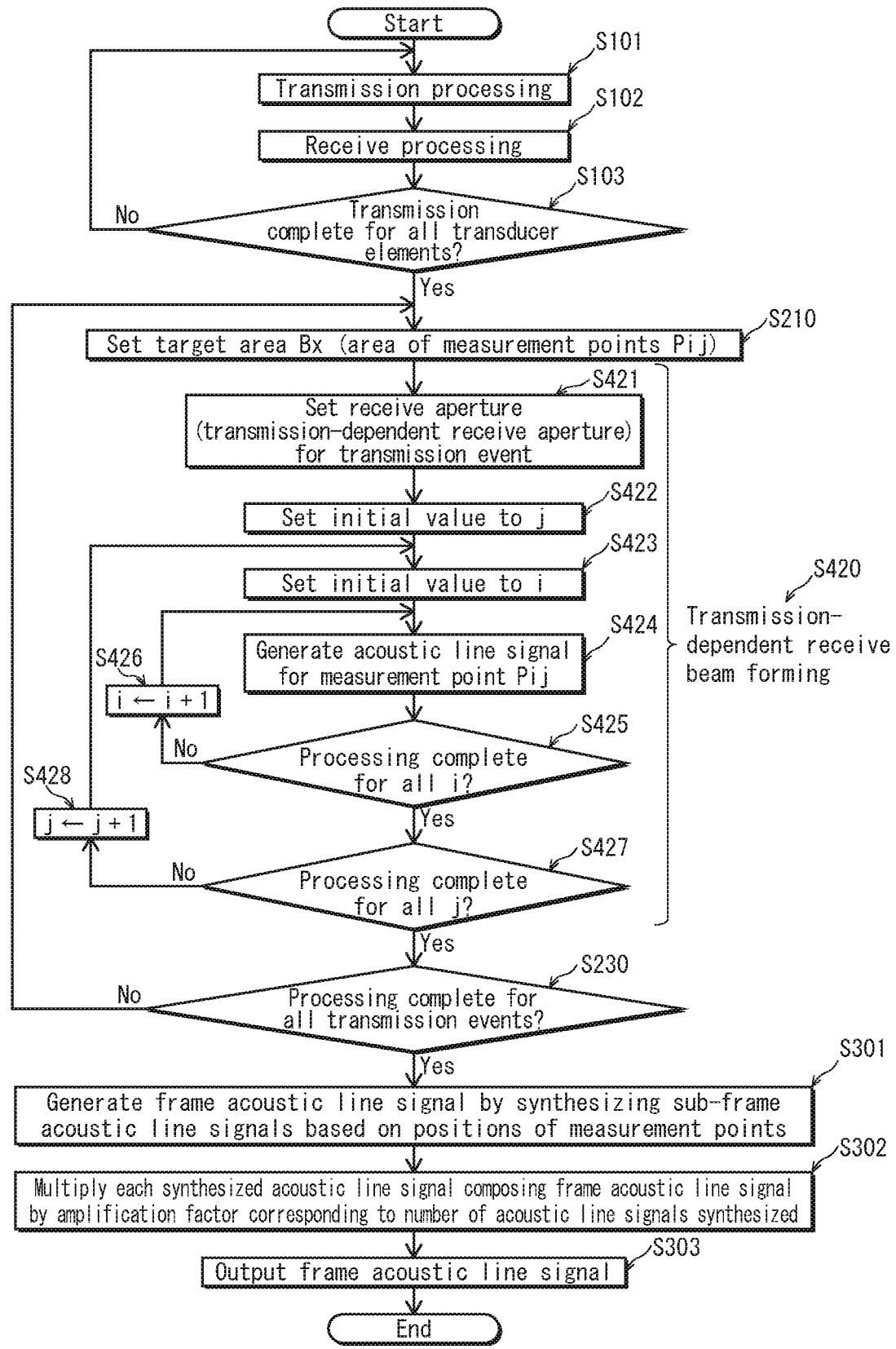
FIG. 19 is a flowchart illustrating operations of an ultrasound diagnostic device pertaining to modification 1 for generating a frame acoustic line signal.

FIG. 19 is a flowchart illustrating frame acoustic line signal generation by the ultrasound diagnostic device pertaining to modification 1. The flowchart in FIG. 19 differs from the flowchart in FIG. 11 for transmission-dependent dependent beam forming (Step S420 (including Steps S421 through S428)) being performed in place of measurement point-dependent beam forming (Step S220 (including Steps S221 through S228)). Meanwhile, the processing in steps other than Step S420 in the flowchart in FIG. 19 is similar to the processing in the corresponding steps in the flowchart in FIG. 11. Thus, description of such similar processing is not provided in the following.

In Step S420, first, the Tx receive aperture setter sets a receive aperture Rx for a transmission event by selecting receive transducer elements Rk composing a receive transducer element array whose center position matches the center position of the transducer element array composing the transmission aperture Tx for the corresponding transmission event, in Step S421.

Figure 20:
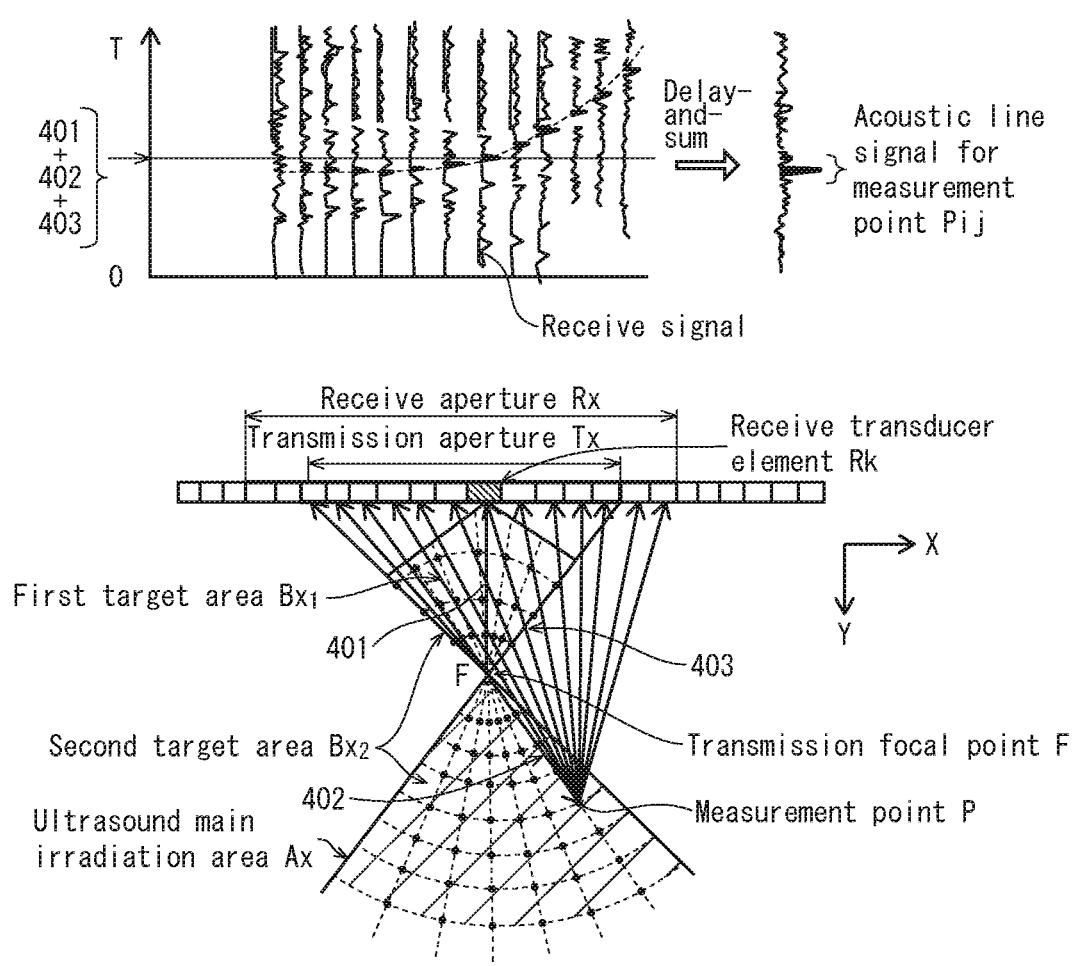
FIG. 20 is a schematic for explaining operations of a receive beam former pertaining to modification 1 for generating an acoustic line signal for a measurement point Pij.

Subsequently, coordinate values i and j indicating a position of a measurement point Pij of the target area Bx for the processing-target transmission event are initialized (set to the respective minimum possible values in the target area Bx set in Step S210) (Steps S422 and S423). Subsequently, an acoustic line signal is generated for the current measurement point Pij (Step S424). FIG. 20 is a schematic for explaining the operations of the receive beam former pertaining to modification 1 for generating the acoustic line signal for the current measurement point Pij. FIG. 20 differs from FIG. 13 referred to in the embodiment in terms of the positional relationship between the transmission aperture Tx and the receive aperture Rx. The processing in Step S424 is similar to that in Step S224 of FIG. 11 (i.e., Steps S2241 through S2251 in FIG. 12).

An acoustic line signal is generated for each measurement point Pij (each illustrated in FIG. 20 as a black dot) of the target area Bx by repeating Step S424 while incrementing the coordinate values i and j. Subsequently, a determination is performed of whether an acoustic line signal has not yet been generated for one or more of the measurement points Pij of the target area Bx (Steps S425, S427). When an acoustic line signal has not yet been generated for every measurement point Pij of the target area Bx, the coordinate values i and j are incremented (Steps S426 and S428), yielding an acoustic line signal for another measurement point Pij (Step S424). Meanwhile, when an acoustic line signal has already been generated for every measurement point Pij of the target area Bx, processing proceeds to Step S230. At this point, an acoustic line signal has already been generated for each measurement point Pij of the target area Bx for the processing-target transmission event, and the acoustic line signals have been output to and stored to the data storage 107.

<Effects>

The ultrasound diagnostic device pertaining to modification 1, which has been described up to this point, achieves the effects described in the embodiment, excluding the effect related to setting a measurement point-dependent receive aperture. In place of the effect related to setting a measurement point-dependent receive aperture, the ultrasound diagnostic device pertaining to modification 1 achieves the following effect. In modification 1, for each transmission event, the receive aperture Rx is set by selecting receive transducer elements forming a transducer element array whose center position corresponds to the center position of the transducer element array composing the transmission aperture Tx for the transmission event. Due to this, the position of the central axis Rxo of the receive aperture Rx for a given transmission event corresponds to the position of the central axis Txo of the transmission aperture Tx for the same transmission event. Further, when transmission events are repetitively performed, the transmission aperture Tx shifts in the transducer element array direction each time, and the receive aperture Rx also shifts in the transducer element array direction in synchronization with the transmission aperture Tx. Thus, a different receive aperture is used to perform delay-and-sum calculation for each transmission event. Accordingly, receive processing with respect to multiple transmission events can be performed by using a group of receive apertures covering a vast measurement area and each differing in terms of time. Thus, uniform spatial resolution is achieved over a vast measurement area.

<Modification 2>

In the ultrasound diagnostic devices pertaining to the embodiment and modification 1, the target area Bx is composed of the first target area $Bx_1$, which is located in the first depth range which is at or shallower than the predetermined depth, and the second target area $Bx_2$, which is located in the second depth range which is deeper than the predetermined depth. Alternatively, the target area Bx may have other shape.

Figure 21A:
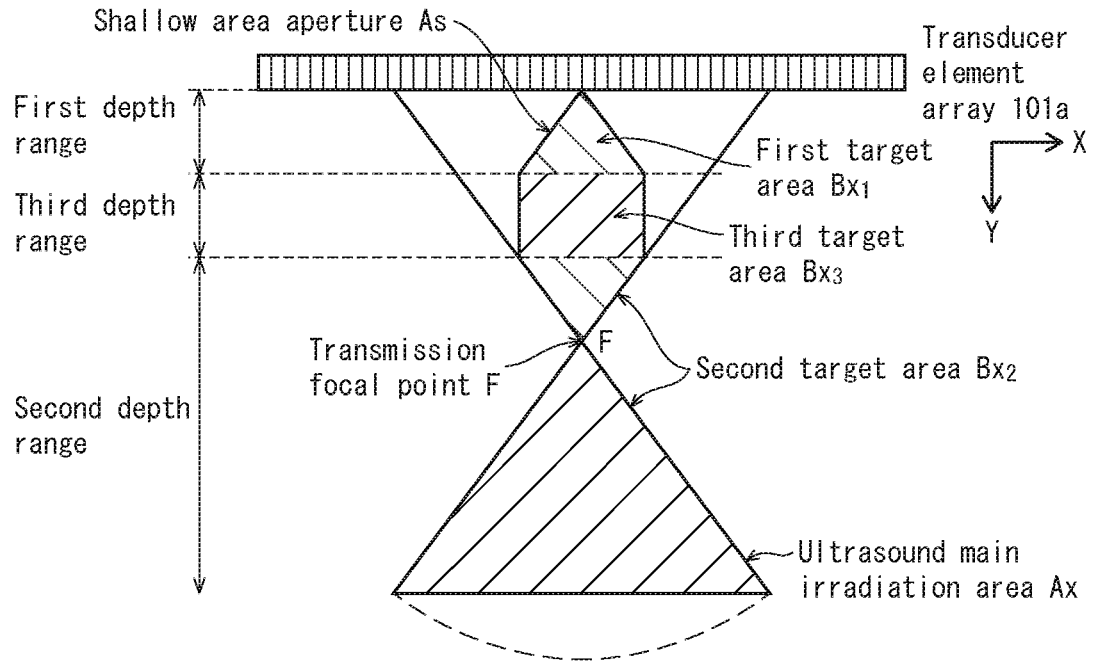
FIGS. 21A to 21C illustrate setting examples of a target area Bx pertaining to modification 2.

FIG. 21A illustrates a first setting example of a target area Bx pertaining to modification 2. As illustrated in FIG. 21A, the target area Bx is composed of a first target area $Bx_1$ located in a first depth range, a second target area $Bx_2$ located in a second depth range, and a third target area $Bx_3$ located in a third depth range between the first depth range and the second depth range. The third target area $Bx_3$ is for example a rectangular area whose width in the transducer element array direction at any depth in the third depth range is equal to the width in the transducer element array direction of the first target area $Bx_1$ at a boundary depth between the first depth range and the third depth range. That is, the target area Bx has, as the maximum width in the transducer element array direction in areas located shallower than the focal depth, the maximum width of the first target area $Bx_1$ in the transducer element array direction. With this structure, it is possible to suppress a decrease in S/N ratio of frame acoustic line signals and reduce the computation amount.

Figure 21B:
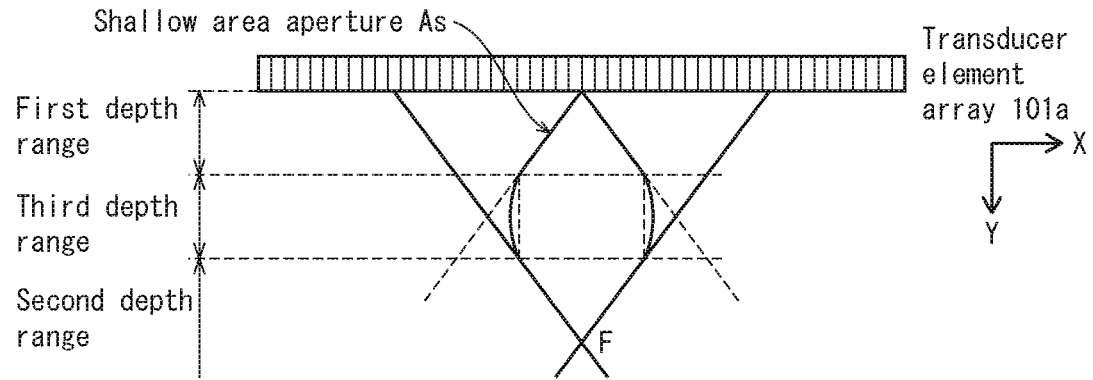
Figure 21C:
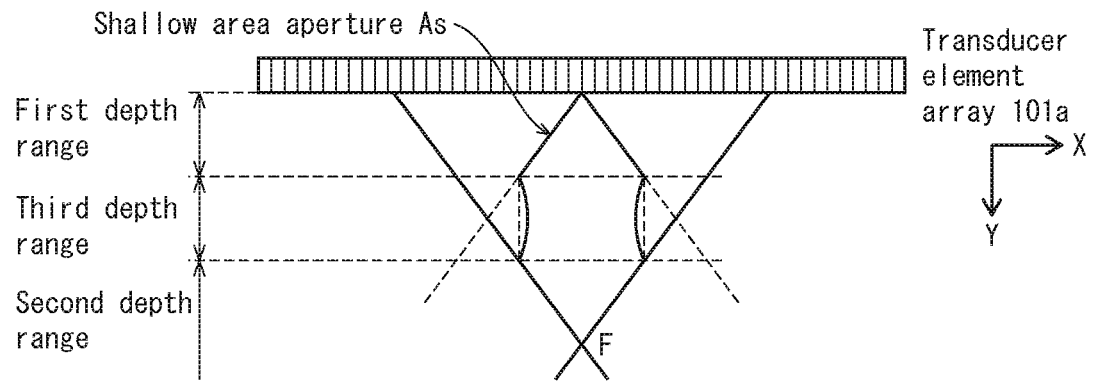

The shape of the third target area $Bx_3$ is not limited to a rectangle. FIG. 21B illustrates a second setting example of the target area Bx pertaining to modification 2. In the second setting example, a first target area $Bx_1$ located in a first depth range and a second target area $Bx_2$ located in a second depth range are the same as those in the first setting example. In contrast, a third target area $Bx_3$ in the second setting example is a barrel-shaped area, as illustrated in FIG. 21B, whose width in the transducer element array direction is large at the middle area relative to the shallowest area and the deepest area. Also, FIG. 21C illustrates a third setting example of the target area Bx pertaining to modification 2. In the third setting example contrary to the second setting example, a third target area $Bx_3$ is a hourglass-shaped area, as illustrated in FIG. 21C, whose width in the transducer element array direction is small at the middle area relative to the shallowest area and the deepest area.

The shape of the third target area $Bx_3$ is not limited to those above examples, and alternatively may be any shape unless the third target area $Bx_3$ is all areas of the ultrasound main irradiation area Ax that are located in the third depth range.

<Modification 3>

In the ultrasound diagnostic devices pertaining to the embodiment and modifications 1 and 2, the target area Bx includes measurement points that are arranged at substantially equal intervals in the transducer element array direction and the depth direction. Alternatively, the target area Bx may have features other than the above.

Figure 22A:
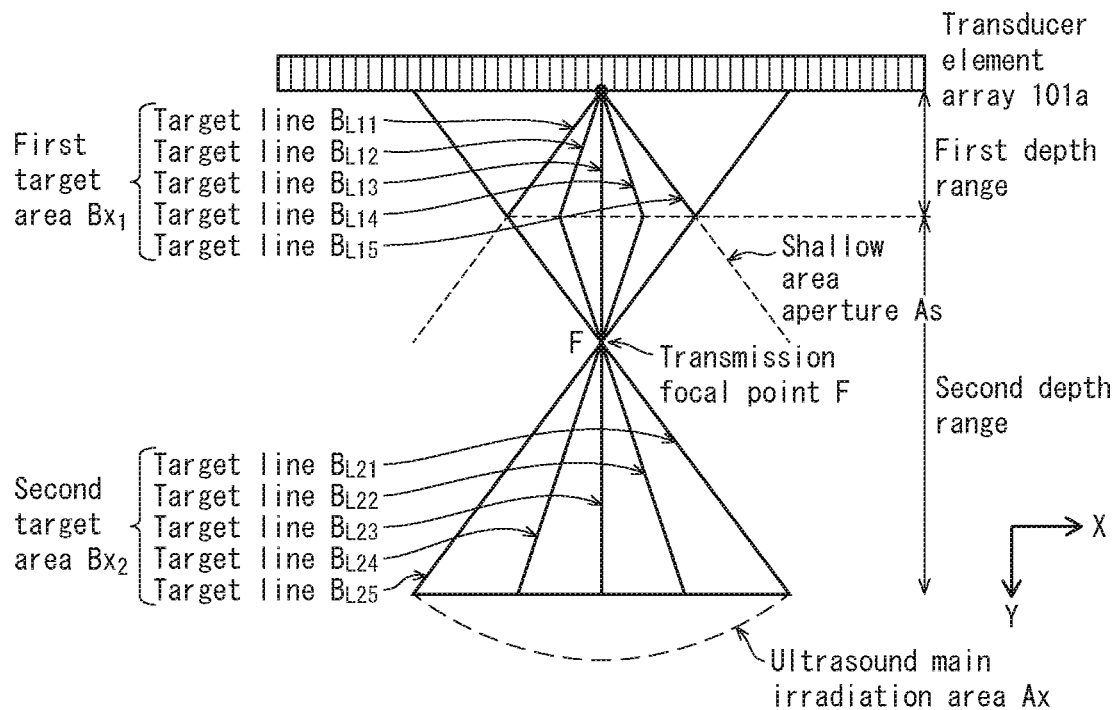
FIGS. 22A and 22B illustrate setting examples of a target area Bx pertaining to modification 3.

FIG. 22A illustrates a first setting example of a target area Bx pertaining to modification 3. In the first setting example, the target area Bx is composed of a first target area $Bx_1$ and a second target area $Bx_2$ like in the embodiment. Specifically, the first target area $Bx_1$ includes areas that are located inside a shallow area aperture As and inside an ultrasound main irradiation area Ax in a first depth range. The second target area $Bx_2$ includes areas that are located inside the ultrasound main irradiation area Ax in a second depth range. Meanwhile, as illustrated in FIG. 22A, the first target area $Bx_1$ is composed of linear areas extending radially from the center of the transmission aperture Tx, namely, target lines $B_{L11}$, $B_{L12}$, $B_{L13}$, $B_{L14}$, and $B_{L15}$. Similarly, the second target area $Bx_2$ is composed of linear areas passing through the focal point F, namely, target lines $B_{L21}$, $B_{L22}$, $B_{L23}$, $B_{L24}$, and $B_{L25}$. That is, in the target area Bx pertaining to modification 3, measurement points are set not in the entirety of the first target area $Bx_1$ but only in the target lines $B_{L11}$, $B_{L12}$, $B_{L13}$, $B_{L14}$, and $B_{L15}$, which are located inside the first target area $Bx_1$. Due to this, the measurement point density in the transducer element array direction is low compared with that in the embodiment. With this structure, it is possible to reduce the computation amount by reducing the number of measurement points while suppressing a decrease of the effect of virtual transmission focusing.

Figure 22B:
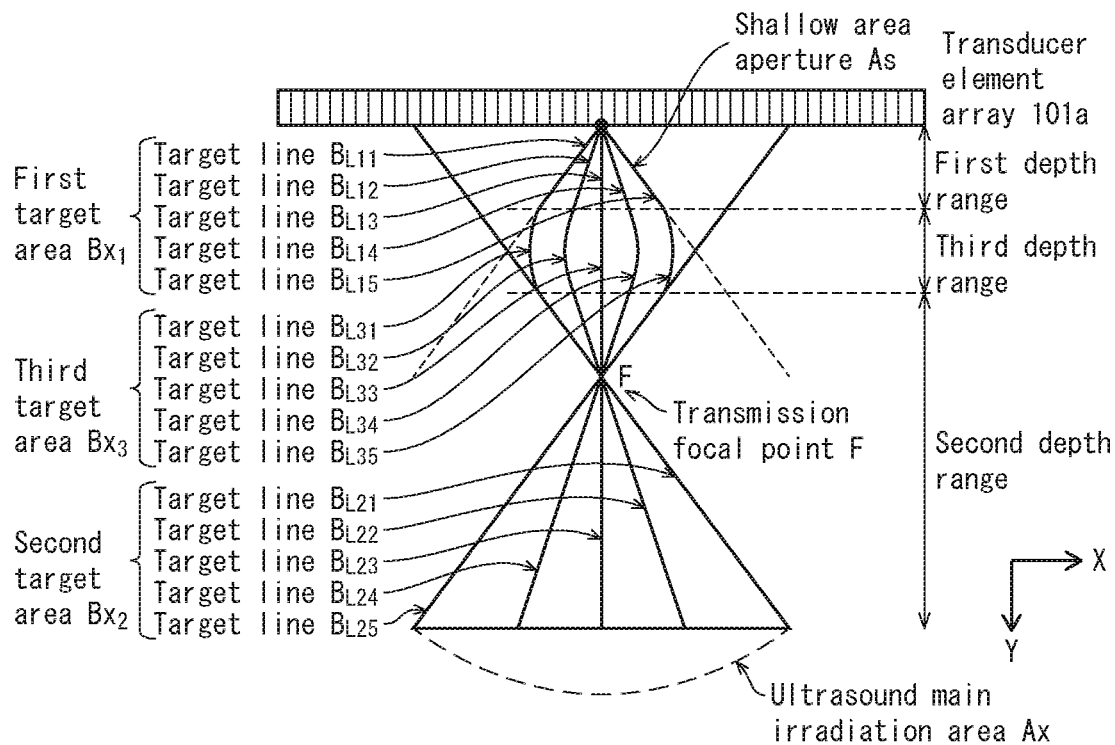

Also, FIG. 22B illustrates a second setting example of the target area Bx pertaining to modification 3. In the second setting example, the target area Bx is composed of a first target area $Bx_1$, a second target area $Bx_2$, and a third target area $Bx_3$ like in the second setting example of modification 2. Specifically, the first target area $Bx_1$ includes areas that are located inside a shallow area aperture As and inside an ultrasound main irradiation area Ax in a first depth range. The second target area $Bx_2$ includes areas that are located inside the ultrasound main irradiation area Ax in a second depth range. The third target area $Bx_3$ includes area that are located inside part of the ultrasound main irradiation area Ax in a third depth range. Meanwhile, as illustrated in FIG. 22B, the first target area $Bx_1$ is composed of linear areas extending radially from the center of the transmission aperture Tx, namely, target lines $B_{L11}$, $B_{L12}$, $B_{L13}$, $B_{L14}$, and $B_{L15}$. Similarly, the second target area $Bx_2$ is composed of linear areas passing through the focal point F, namely, target lines $B_{L21}$, $B_{L22}$, $B_{L23}$, $B_{L24}$, and $B_{L25}$. Also, the third target area $Bx_3$ is composed of a target line $B_{L31}$ that is located between the target lines $B_{L11}$ and $B_{L21}$, a target line $B_{L32}$ that is located between the target lines $B_{L12}$ and $B_{L22}$, a target line $B_{L33}$ that is located between the target lines $B_{L13}$ and $B_{L23}$, a target line $B_{L34}$ that is located between the target lines $B_{L14}$ and $B_{L24}$, and a target line L35 that is located between the target lines $B_{L15}$ and $B_{L25}$. Due to this, the measurement point density in the transducer element array direction for the second setting example of modification 3 is also low compared with that in modification 2. With this structure, it is possible to reduce the computation amount by reducing the number of measurement points while suppressing a decrease of the effect of virtual transmission focusing.

In the above examples, the first target area $Bx_1$, the second target area $Bx_2$, and the third target area $Bx_3$ are each composed of five target lines. Alternatively, these target areas may be composed of any same number of target lines. Also, the target lines should preferably be located such that measurement points on the target lines are spaced away from one another at equal distance in the transducer element array direction. Alternatively, the target lines may be located such that every pair of adjacent ones of the target lines forms a predetermined angle therebetween. Further, the target lines may be located such that the distance between measurement points in the transducer element array direction decreases as approaching the central axis Txo of the transmission aperture Tx, and increases as departing the central axis Txo. Moreover, the first target area $Bx_1$, the second target area $Bx_2$, and the third target area $Bx_3$ each may be composed of a different number of target lines.

<Modification 4>

The ultrasound diagnostic devices pertaining to the embodiment and modifications 1 to 3 transmit, as ultrasound beams, waves focusing on the transmission focal point F or waves converging within a range having a small width in the transducer element array direction around the transmission focal point F. Alternatively, ultrasound beams to be transmitted may be unconverging waves such as plane waves.

Figure 23A:
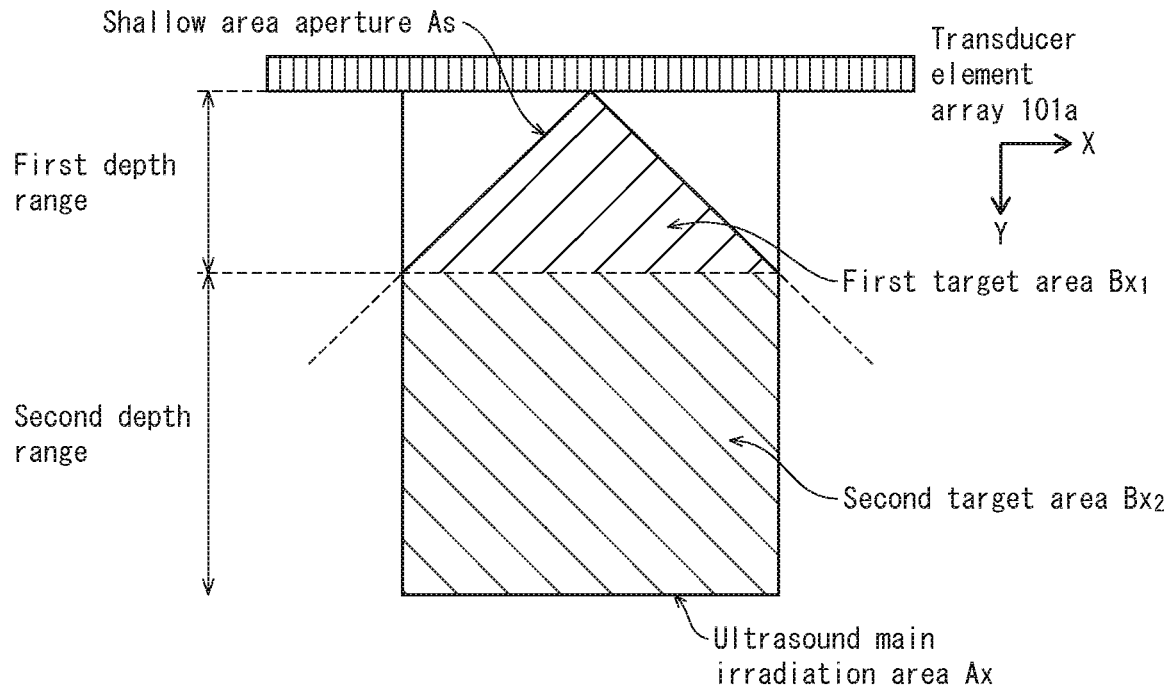
FIGS. 23A and 23B illustrate setting examples of a target area Bx pertaining to modification 4.

FIG. 23A illustrates a first setting example of a target area Bx pertaining to modification 4. In the first setting example, ultrasound beams are plane waves, and an ultrasound main irradiation area Ax is a rectangular area having sides, one of which coincides with the transmission aperture Tx. Here, a shallow area aperture As is set in the same manner as in the embodiment and so on. A first target area $Bx_1$ is set so as to be located inside the shallow area aperture As and the ultrasound main irradiation area Ax in the first depth range. Also, a second target area $Bx_2$ set so as to be located inside the ultrasound main irradiation area Ax in the second depth range. With this structure, by excluding measurement points for which the S/N ratio is not sufficiently improved even by delay-and-sum calculation from the target area, it is possible to reduce delay-and-sum calculation amount while minimalizing the influence of degradation of frame acoustic line signal quality.

Figure 23B:
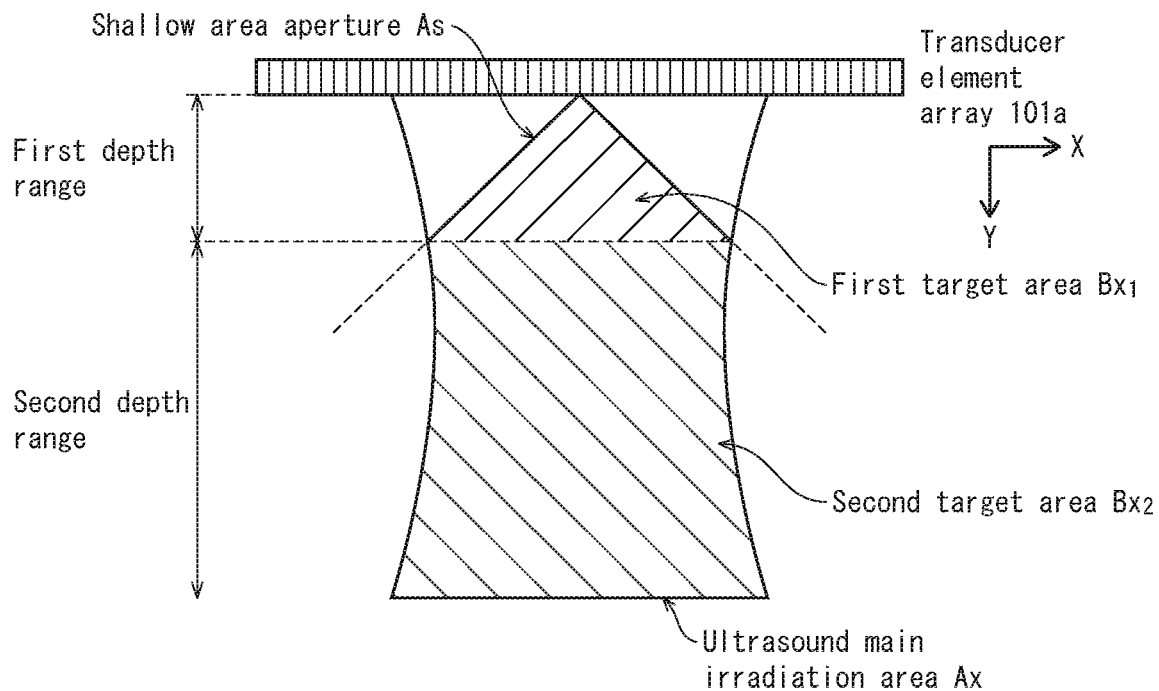

Also, FIG. 23B illustrates a second setting example of the target area Bx pertaining to modification 4. In the second setting example, ultrasound beams are so-called fat beams converging within areas that are large enough for the beams to be regarded as unconverging waves. An ultrasound main irradiation area Ax is a substantially rectangular area having sides, one of which coincides with the transmission aperture Tx, and having a middle part whose width in the transducer element array direction is slightly small. Here, a shallow area aperture As is set in the same manner as in the embodiment and so on. A first target area $Bx_1$ is set so as to be located inside the shallow area aperture As and the ultrasound main irradiation area Ax in the first depth range. Also, a second target area $Bx_2$ is set so as to be located inside the ultrasound main irradiation area Ax in the second depth range. With this structure, by excluding the measurement points for which the S/N ratio is not sufficiently improved even by delay-and-sum calculation from the target area, it is possible to reduce delay-and-sum calculation amount while minimalizing the influence of degradation of frame acoustic line signal quality.

Figure 24A:
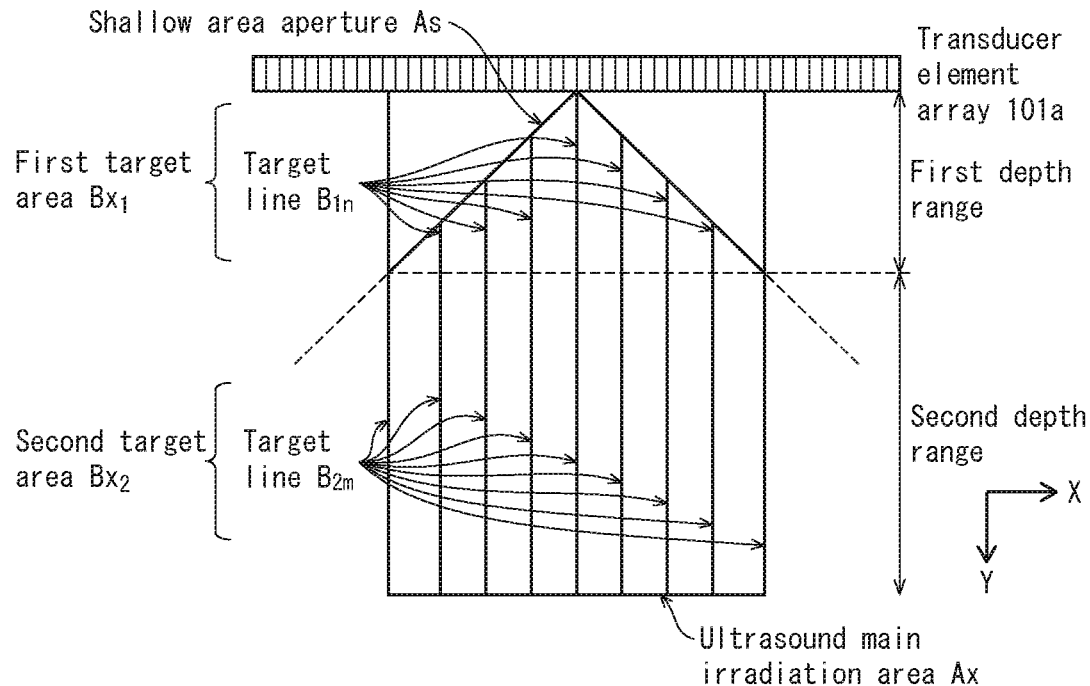
FIGS. 24A and 24B illustrate setting examples of the target area Bx pertaining to modification 4.
Figure 24B:
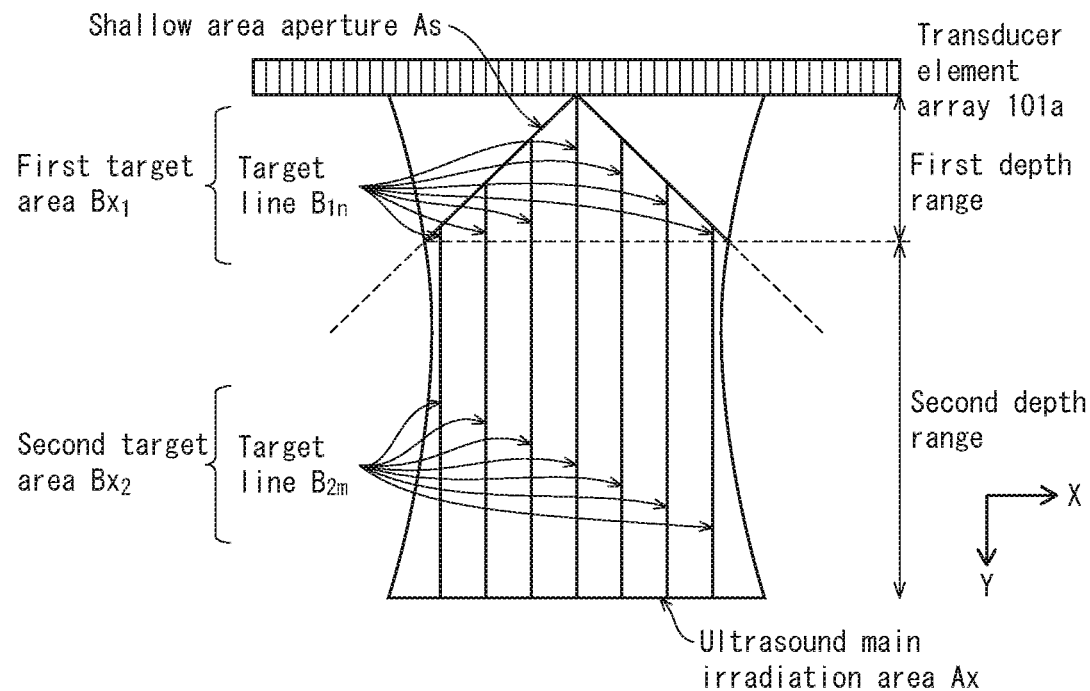

As illustrated FIG. 24A, the first setting example may be combined with modification 3, where the first target area $Bx_1$ may be composed of linear areas extending in the depth direction, namely, target lines $B_{Ln}$, and the second target area $Bx_2$ may be composed of linear areas extending in the depth direction, namely, target lines $B_{L2m}$. Similarly, as illustrated FIG. 24B, the second setting example may be combined with modification 3, where the first target area $Bx_1$ may be composed of linear areas extending in the depth direction, namely, target lines $B_{Ln}$, and the second target area $Bx_2$ may be composed of linear areas extending in the depth direction, namely, target lines $B_{L2m}$.

Also, though not illustrated, the first or second setting example may be combined with modification 2, where a third target area $Bx_3$ is set in addition to the first target area $Bx_1$ and the second target area $Bx_2$.

<Other Modifications>

(1) In the embodiment and the modifications, the first target area $Bx_1$, the second target area $Bx_2$, and the third target area $Bx_3$ are equal to each other in terms of measurement point density. Alternatively, the first target area $Bx_1$, the second target area $Bx_2$, and the third target area $Bx_3$ may for example differ from each other in terms of measurement point density. In this case, as described in modification 3, by decreasing the measurement point density in the transducer element array direction without changing the measurement point density in the depth direction, it is possible to suppress the decrease of spatial resolution and S/N ratio of frame acoustic line signals even with a greatly reduced computation amount. For example, the measurement point density in the transducer element array direction only in the second target area $Bx_2$ may be decreased. With this structure, with respect to measurement points at deeper depths from which weak reflected ultrasound is acquired, it is possible to suppress an increase in computation amount in the case where low effects of spatial resolution and S/N ratio of frame acoustic line signals are exhibited by increasing the synthesizing number of acoustic line signals.

(2) In the embodiment and the modifications, the second target area $Bx_2$ is all areas of the ultrasound main irradiation area Ax that are located in the second depth range. Alternatively, the second target area $Bx_2$ may be for example part of the ultrasound main irradiation area Ax in the second depth range. For example, the second target area $Bx_2$ may be part of the ultrasound main irradiation area Ax in the transducer element array direction in the second depth range. Specifically, the second target area $Bx_2$ may be a triangular area resulting from narrowing the width of the ultrasound main irradiation area Ax in the transducer element array direction in the second depth range. Further alternatively, the second target area $Bx_2$ may have a shape like a combination of a triangle and a quadrangle. Specifically, the second target area $Bx_2$ may include, at depths at the predetermined depth or shallower, a triangular area in the ultrasound main irradiation area Ax whose width in the transducer element array direction is a predetermined width or smaller, and include, at depths deeper than the predetermined depth, a quadrangle area whose width is equal to the width of the triangular area at the predetermined depth. Yet alternatively, the second target area $Bx_2$ may for example have, at depths deeper than the predetermined depth, a width in the transducer element array direction that decreases towards deeper depths. With this structure, with respect to measurement points at deeper depths from which weak reflected ultrasound is acquired, it is possible to suppress an increase in computation amount in the case where low effects of spatial resolution and S/N ratio of frame acoustic line signals are exhibited by increasing the synthesizing number of acoustic line signals.

(3) In the embodiment and the modifications, the shallow area aperture As is determined based on frequency of ultrasound that is a transmission and reception target and information indicating directional characteristic of the ultrasound probe 101 or directional characteristic of the transducer elements 101a. Alternatively, information for determining the shallow area aperture As may include other conditions for ultrasound transmission such as wave number, transmission time, and transmission intervals. Also, the information indicating the directional characteristic of the ultrasound probe 101 or the directional characteristic of the transducer elements 101a may be managed in association with a model number or the like of the ultrasound probe 101.

(4) Up to this point, the present disclosure has been described based on the embodiment and the modifications. However, the embodiment and the modification described above are non-limiting examples of application of the present disclosure, and thus the present invention shall be construed to encompass the following exemplar modifications.

For example, the present invention may be implemented by using a computer system including a memory storing a computer program and a microprocessor operating based on the computer program. For example, the computer system may store a computer program of the ultrasound signal processing method pertaining to the present invention, and the computer system may operate in accordance with the computer program or may provide instructions in accordance with the computer program to various components connected thereto.

Further, the present invention may be implemented by implementing a part of or the entirety of the ultrasound signal processing device described above, or a part of or an entirety of a beam former described above by using a computer system including a microprocessor, a recording medium such as a ROM or a RAM, and a hard disk unit. In this implementation, a computer program achieving the same operations as a device described above is stored to the RAM or the hard disk unit. Further, in this implementation, various devices achieve their functions by the microprocessor operating in accordance with the computer program.

Further, the present invention may be implemented by implementing some or all components included in a device described above by using one system LSI (large scale integration). A system LSI is an ultra-multifunctional LSI manufactured by integrating multiple components onto one chip. Specifically, a system LSI is a computer system including a microprocessor, a ROM, a RAM, and the like. Further, each component may be separately implemented by using one chip, or some or all components may be implemented by using one chip. Note that LSIs are referred to by using different names, depending upon the level of integration achieved thereby. Such names include IC, system LSI, super LSI, and ultra LSI. In this implementation, a computer program achieving the same operations as any device described above is stored to the RAM. Further, in this implementation, the system LSI achieves its functions by the microprocessor operating in accordance with the computer program. For example, the present invention encompasses a form of implementation where an LSI stores a beam forming method pertaining to the present invention as a program, the LSI is inserted into a computer, and the computer executes the program (i.e., the beam forming method pertaining to the present invention).

Note that integration of circuits may be achieved by a dedicated circuit or a general purpose processor, in addition to being achievable by using an LSI as discussed above. Further, a Field Programmable Gate Array (FPGA), which is programmable after manufacturing, or a reconfigurable processor, which allows reconfiguration of the connection and setting of circuit cells inside the LSI, may be used.

Furthermore, if technology for circuit integration that replaces LSIs emerges, owing to advances in semiconductor technology or to another derivative technology, the integration of functional blocks may naturally be accomplished using such technology.

Further, some or all functions of an ultrasound diagnostic device discussed in the embodiment may be implemented by a processor such as a CPU executing a program. Further, the present invention may be implemented by using a non-transitory computer-readable recording medium having recorded thereon a program causing execution of a diagnostic method and a beam forming method of an ultrasound diagnostic device. Further, execution of the program by another independent computer system may be achieved by transferring the program by recording the program or a signal onto a recording medium. Naturally, the program may be distributed via means of transmission media such as the internet.

The ultrasound diagnostic device pertaining to the embodiment includes the data storage, which is a recording device. However, the recording device need not be included in the ultrasound diagnostic device, and may be implemented by using a semiconductor memory, a hard disk drive, an optical disk drive, a magnetic storage device, or the like connected to the ultrasound diagnostic device from the outside.

Further, the functional blocks illustrated in the block diagrams are mere examples of possible functional blocks. That is, a plurality of functional blocks illustrated in the block diagrams may be combined to form one functional block, a given functional block illustrated in the block diagrams may be divided into a plurality of functional blocks, and a function of a given functional block illustrated in the block diagrams may be transferred to another functional block. Further, with regards to multiple functional blocks having similar functions, such functional blocks may be implemented by one piece of hardware or software executing such functions in parallel or by applying time division.

Further, the above-described order in which steps of processing are executed is a non-limiting example among multiple possible orders that is used for the sole sake of providing specific description of the present invention. Further, some of the steps of processing described above may be executed simultaneously (in parallel).

Further, in the embodiment, description is provided that the ultrasound diagnostic device may have a probe and a display attached thereto. However, the ultrasound diagnostic device may include a probe and a display therein.

Further, in the embodiment, the probe includes a plurality of piezoelectric transducer elements forming a line one-dimensionally. However, the probe may have a different structure. For example, the probe may include a plurality of piezoelectric transducer elements disposed two-dimensionally. Alternatively, the probe may be a swingable probe including a plurality of swingable transducer elements (i.e., transducer elements that can be caused to swing by mechanical means) forming a line one-dimensionally, which enables acquisition of three-dimensional tomographic images. Further, probes of different types may be selected and used depending upon the examination to be performed. For example, when using a probe including piezoelectric transducer elements disposed two-dimensionally, supplying different piezoelectric transducer elements with voltages at different timings or with voltages with different values achieves controlling the position, the direction, etc., of the ultrasound beam to be transmitted.

Further, the probe may be provided with some of the functions of a transmission beam former/receive beam former. For example, the probe may be capable of generating a transmission electric signal based on a control signal that the transmission beam former/receive beam former outputs to cause generation of a transmission electric signal, and of converting the transmission electronic signal into ultrasound. In addition, the probe may be capable of converting reflected ultrasound into a receive electric signal, and of generating a receive signal based on the receive electric signal.

Further, at least some of the functions of the ultrasound diagnostic devices pertaining to the embodiment and the modification may be combined with functions of other ones of the ultrasound diagnostic devices pertaining to the embodiment and the modification. Further, the values used above are non-limiting examples used for the sole sake of providing specific description of the present invention, and may be replaced with other values.

Further, the present invention should be construed as encompassing various modifications that a skilled artisan would arrive at based on the embodiment describe above.

<Review>

(1) An ultrasound signal processing device pertaining to at least one embodiment is an ultrasound signal processing device that performs transmission events of transmitting ultrasound beams to a subject by using an ultrasound probe having transducer elements, generates a sub-frame acoustic line signal for each of the transmission events based on signals acquired through reception of reflected ultrasound from the subject by the ultrasound probe, and synthesizes sub-frame acoustic line signals for the respective transmission events to generate a frame acoustic line signal. The ultrasound signal processing device includes ultrasound signal processing circuitry including: a transmitter that, for each of the transmission events, shifts a transmission aperture including part of the transducer elements in a transducer element array direction in which the transducer elements are arrayed, and causes the ultrasound probe to transmit ultrasound beams to an ultrasound main irradiation area defined by a position of the transmission aperture; a receiver that, for each of the transmission events, generates sequences of receive signals for at least part of the transducer elements based on reflected ultrasound received by the ultrasound probe from the subject; a delay-and-sum calculator that, for each of the transmission events, sets a target area in the ultrasound main irradiation area, and performs delay-and-sum calculation with respect to the sequences of receive signals from measurement points located in the target area to generate a sub-frame acoustic line signal, the target area having, in a depth range shallower than a focal point, a width in the transducer element array direction that decreases as the depth decreases; and a synthesizer that synthesizes sub-frame acoustic line signals for the transmission events to generate a frame acoustic line signal.

Also, an ultrasound signal processing method pertaining to at least one embodiment is an ultrasound signal processing method of performing transmission events of transmitting ultrasound beams to a subject by using an ultrasound probe having transducer elements, generating a sub-frame acoustic line signal for each of the transmission events based on signals acquired through reception of reflected ultrasound from the subject by the ultrasound probe, and synthesizing sub-frame acoustic line signals for the respective transmission events to generate a frame acoustic line signal. The ultrasound signal processing method includes: for each of the transmission events, shifting a transmission aperture including part of the transducer elements in a transducer element array direction in which the transducer elements are arrayed, and causing the ultrasound probe to transmit ultrasound beams to an ultrasound main irradiation area defined by a position of the transmission aperture; for each of the transmission events, generating sequences of receive signals for at least part of the transducer elements based on reflected ultrasound received by the ultrasound probe from the subject; for each of the transmission events, setting a target area in the ultrasound main irradiation area, and performing delay-and-sum calculation with respect to the sequences of receive signals from measurement points located in the target area to generate a sub-frame acoustic line signal, the target area having, in a depth range shallower than a focal point, a width in the transducer element array direction that decreases as the depth decreases; and synthesizing sub-frame acoustic line signals for the transmission events to generate a frame acoustic line signal.

With the above structure or method, it is possible to set, in a depth range shallower than a focal point, a measurement point and each of receive transducer elements receiving reflected ultrasound from the measurement point so as to be close to each other, thereby improving spatial resolution and S/N ratio of acoustic line signals. Also, it is possible to set, in depths other than the depth range, a large width of the target area in the transducer element array direction, thereby improving the spatial resolution and the S/N ratio by virtual transmission focusing.

(2) An ultrasound signal processing device pertaining to at least one embodiment is an ultrasound signal processing device that performs transmission events of transmitting converging ultrasound beams to a subject by using an ultrasound probe having transducer elements, generates a sub-frame acoustic line signal for each of the transmission events based on signals acquired through reception of reflected ultrasound from the subject by the ultrasound probe, and synthesizes sub-frame acoustic line signals for the respective transmission events to generate a frame acoustic line signal. The ultrasound signal processing device includes ultrasound signal processing circuitry including: a transmitter that, for each of the transmission events, shifts a transmission aperture including part of the transducer elements in a transducer element array direction in which the transducer elements are arrayed, and causes the ultrasound probe to transmit ultrasound beams to an ultrasound main irradiation area so that the ultrasound beams converges at a focal point defined by a position of the transmission aperture; a receiver that, for each of the transmission events, generates sequences of receive signals for at least part of the transducer elements based on reflected ultrasound received by the ultrasound probe from the subject; a delay-and-sum calculator that, for each of the transmission events, sets a target area in the ultrasound main irradiation area, and performs delay-and-sum calculation with respect to the sequences of receive signals from measurement points located in the target area to generate a sub-frame acoustic line signal, the target area having, in a predetermined depth range shallower than the focal point, a width in the transducer element array direction that decreases as the depth decreases; and a synthesizer that synthesizes sub-frame acoustic line signals for the transmission events to generate a frame acoustic line signal.

Also, an ultrasound signal processing method pertaining to at least one embodiment is an ultrasound signal processing method of performing transmission events of transmitting converging ultrasound beams to a subject by using an ultrasound probe having transducer elements, generating a sub-frame acoustic line signal for each of the transmission events based on signals acquired through reception of reflected ultrasound from the subject by the ultrasound probe, and synthesizing sub-frame acoustic line signals for the respective transmission events to generate a frame acoustic line signal. The ultrasound signal processing method includes: for each of the transmission events, shifting a transmission aperture including part of the transducer elements in a transducer element array direction in which the transducer elements are arrayed, and causing the ultrasound probe to transmit ultrasound beams to an ultrasound main irradiation area so that the ultrasound beams converges at a focal point defined by a position of the transmission aperture; for each of the transmission events, generating sequences of receive signals for at least part of the transducer elements based on reflected ultrasound received by the ultrasound probe from the subject; for each of the transmission events, setting a target area in the ultrasound main irradiation area, and performing delay-and-sum calculation with respect to the sequences of receive signals from measurement points located in the target area to generate a sub-frame acoustic line signal, the target area having, in a predetermined depth range shallower than the focal point, a width in the transducer element array direction that decreases as the depth decreases; and synthesizing sub-frame acoustic line signals for the transmission events to generate a frame acoustic line signal.

Even with the above structure or method, it is possible to set, in a depth range shallower than a focal point, a measurement point and each of receive transducer elements receiving reflected ultrasound from the measurement point so as to be close to each other, thereby improving spatial resolution and S/N ratio of acoustic line signals. Also, it is possible to set, in depths other than the depth range, a large width of the target area in the transducer element array direction, thereby improving the spatial resolution and the S/N ratio by virtual transmission focusing.

(3) Also, according to the ultrasound signal processing device of the above section (1) or (2), the target area may include all areas of the ultrasound main irradiation area that are located in a second depth range deeper than the depth range.

With the above structure, in depths other than the depth range, it is possible to maximize the use efficiency of ultrasound and improve the spatial resolution and the S/N ratio by virtual transmission focusing.

(4) Also, according to the ultrasound signal processing device of the above sections (1) to (3), the target area may have, in the depth range, a width in the transducer element array direction that is proportional to the depth.

With the above structure, in the depth range, it is possible to set the shape of the target area by a simple method such that the width in the transducer element array direction decreases as the depth decreases.

(5) Also, according to the ultrasound signal processing device of the above sections (1) to (3), the target area may have, in the depth range, a shape determined based on directional characteristics of the transducer elements.

With the above structure, it is possible to set, in the depth range, the shape of the target area based on reception characteristics of the transducer elements.

(6) Also, according to the ultrasound signal processing device of the above sections (1) to (3), the target area may have, in the depth range, a shape determined based on a reception beam profile of the ultrasound probe.

With the above structure, it is possible to set, in the depth range, the shape of the target area based on reception characteristics of the ultrasound probe.

(7) Also, according to the ultrasound signal processing device of the above section (3), the target area may have, in a third depth range deeper than the depth range and shallower than the second depth range, a smaller width in the transducer element array direction than the ultrasound main irradiation area and a different shape from a shape in the depth range.

With the above structure, it is possible to reduce the number of measurement points in the third width range to reduce the computation amount while suppressing a decrease in the spatial resolution and the S/N ratio of acoustic line signals.

(8) Also, according to the ultrasound signal processing device of the above sections (1) to (7), the ultrasound signal processing circuitry may further include: a parameter holder that holds therein parameter combinations of parameters for determining a shape of the target area; and a target area determiner that acquires the parameter combinations held in the parameter holder, and selects one of the parameter combinations to determine the shape of the target area based on the selected parameter combination.

With the above structure, it is possible to set the shape of the target area based on imaging conditions and the like.

(9) Also, according to the ultrasound signal processing device of the above section (8) the parameters may include at least one of a characteristic value of the ultrasound probe and characteristic values of the transducer elements, and the target area determiner may determine the shape of the target area based on information specifying the ultrasound probe.

With the above structure, it is possible to easily set the shape of the target area based on characteristics of the ultrasound probe or the transducer elements included therein.

(10) Also, according to the ultrasound signal processing device of the above section (8) or (9), the parameters may include at least one of frequency, wave number, time length, and information specifying a transmission beam forming method of the ultrasound beams, and the target area determiner may determine the shape of the target area based on information specifying the ultrasound beams.

With the above structure, it is possible to set the shape of the target area based on characteristics of ultrasound for transmission and reception.

(11) Also, an ultrasound signal processing device pertaining to at least one embodiment includes an ultrasound probe; and the ultrasound signal processing device of the above sections (1) to (10).

Although one or more embodiments of the present invention have been described and illustrated in detail, the disclosed embodiments are made for the purposes of illustration and example only and not limitation. The scope of the present invention should be interpreted by the terms of the appended claims.

What is claimed is:

1. An ultrasound signal processing device that performs transmission events of transmitting ultrasound beams to a subject by using an ultrasound probe having transducer elements, generates a sub-frame acoustic line signal for each of the transmission events based on signals acquired through reception of reflected ultrasound from the subject by the ultrasound probe, and synthesizes sub-frame acoustic line signals for the respective transmission events to generate a frame acoustic line signal, the ultrasound signal processing device comprising ultrasound signal processing circuitry comprising:
a transmitter that, for each of the transmission events, shifts a transmission aperture including part of the transducer elements in a transducer element array direction in which the transducer elements are arrayed, and causes the ultrasound probe to transmit ultrasound beams to an ultrasound main irradiation area defined by a position of the transmission aperture;
a receiver that, for each of the transmission events, generates sequences of receive signals for at least part of the transducer elements based on reflected ultrasound received by the ultrasound probe from the subject;
a delay-and-sum calculator that, for each of the transmission events, sets a target area in the ultrasound main irradiation area, and performs delay-and-sum calculation with respect to the sequences of receive signals from measurement points located in the target area to generate a sub-frame acoustic line signal, wherein the target area is smaller than the ultrasound main irradiation area in a depth range shallower than a focal point of the ultrasound main irradiation area and delay-and-sum calculation is not performed on receive signals from measurement points in the ultrasound main irradiation area that are outside of the target area, the target area has a width in the transducer element array direction that decreases as the depth decreases in the depth range, and the target area is defined by the ultrasound main irradiation area in a second depth range deeper than the depth range and the second depth range of the target area includes an area between the depth range and the focal point; and
a synthesizer that synthesizes sub-frame acoustic line signals for the transmission events to generate a frame acoustic line signal.

2. The ultrasound signal processing device of claim 1, wherein
the target area includes all areas of the ultrasound main irradiation area that are located in a second depth range deeper than the depth range.

3. The ultrasound signal processing device of claim 1, wherein
the target area has, in the depth range, a width in the transducer element array direction that is proportional to the depth.

4. The ultrasound signal processing device of claim 1, wherein
the target area has, in the depth range, a shape determined based on directional characteristics of the transducer elements.

5. The ultrasound signal processing device of claim 1, wherein
the target area has, in the depth range, a shape determined based on a reception beam profile of the ultrasound probe.

6. The ultrasound signal processing device of claim 2, wherein
the target area has, in a third depth range deeper than the depth range and shallower than the second depth range, a smaller width in the transducer element array direction than the ultrasound main irradiation area and a different shape from a shape in the depth range.

7. The ultrasound signal processing device of claim 1, wherein
the delay-and-sum calculator further comprises:
a target area setter that holds therein parameter combinations of parameters for determining a shape of the target area and selects one of the parameter combinations to determine the shape of the target area based on the selected parameter combination.

8. The ultrasound signal processing device of claim 7, wherein
the parameters include at least one of a characteristic value of the ultrasound probe and characteristic values of the transducer elements, and
the target area setter determines the shape of the target area based on information specifying the ultrasound probe.

9. The ultrasound signal processing device of claim 7, wherein
the parameters include at least one of frequency, wave number, time length, and information specifying a transmission beam forming method of the ultrasound beams, and
the target area setter determines the shape of the target area based on information specifying the ultrasound beams.

10. An ultrasound diagnostic device comprising:
an ultrasound probe; and
the ultrasound signal processing device of claim 1.

11. The ultrasound signal processing device of claim 1, wherein
the target area in the depth range shallower than the focal point is an isosceles triangle with a vertex of the isosceles triangle located at a transmission basis point, which is a center of the transmission aperture.

12. An ultrasound signal processing device that performs transmission events of transmitting converging ultrasound beams to a subject by using an ultrasound probe having transducer elements, generates a sub-frame acoustic line signal for each of the transmission events based on signals acquired through reception of reflected ultrasound from the subject by the ultrasound probe, and synthesizes sub-frame acoustic line signals for the respective transmission events to generate a frame acoustic line signal, the ultrasound signal processing device comprising ultrasound signal processing circuitry comprising:
a transmitter that, for each of the transmission events, shifts a transmission aperture including part of the transducer elements in a transducer element array direction in which the transducer elements are arrayed, and causes the ultrasound probe to transmit ultrasound beams to an ultrasound main irradiation area so that the ultrasound beams converge at a focal point defined by a position of the transmission aperture;
a receiver that, for each of the transmission events, generates sequences of receive signals for at least part of the transducer elements based on reflected ultrasound received by the ultrasound probe from the subject;
a delay-and-sum calculator that, for each of the transmission events, sets a target area in the ultrasound main irradiation area, and performs delay-and-sum calculation with respect to the sequences of receive signals from measurement points located in the target area to generate a sub-frame acoustic line signal, wherein the target area is smaller than the ultrasound main irradiation area in a depth range shallower than a focal point of the ultrasound main irradiation area and delay-and-sum calculation is not performed on receive signals from measurement points in the ultrasound main irradiation area that are outside of the target area, the target area has a width in the transducer element array direction that decreases as the depth decreases, wherein the target area is defined by the ultrasound main irradiation area in a second depth range deeper than the depth range and the second depth range of the target area includes an area between the depth range and the focal point; and a synthesizer that synthesizes sub-frame acoustic line signals for the transmission events to generate a frame acoustic line signal.

13. An ultrasound signal processing method of performing transmission events of transmitting ultrasound beams to a subject by using an ultrasound probe having transducer elements, generating a sub-frame acoustic line signal for each of the transmission events based on signals acquired through reception of reflected ultrasound from the subject by the ultrasound probe, and synthesizing sub-frame acoustic line signals for the respective transmission events to generate a frame acoustic line signal, the ultrasound signal processing method comprising:

for each of the transmission events, shifting a transmission aperture including part of the transducer elements in a transducer element array direction in which the transducer elements are arrayed, and causing the ultrasound probe to transmit ultrasound beams to an ultrasound main irradiation area defined by a position of the transmission aperture;

for each of the transmission events, generating sequences of receive signals for at least part of the transducer elements based on reflected ultrasound received by the ultrasound probe from the subject;

for each of the transmission events, setting a target area in the ultrasound main irradiation area, and performing delay-and-sum calculation with respect to the sequences of receive signals from measurement points located in the target area to generate a sub-frame acoustic line signal, wherein the target area is smaller than the ultrasound main irradiation area in a depth range shallower than a focal point of the ultrasound main irradiation area and delay-and-sum calculation is not performed on receive signals from measurement points in the ultrasound main irradiation area that are outside of the target area, the target area has a width in the transducer element array direction that decreases as the depth decreases, wherein the target area is defined by the ultrasound main irradiation area in a second depth range deeper than the depth range and the second depth range of the target area includes an area between the depth range and the focal point; and synthesizing sub-frame acoustic line signals for the transmission events to generate a frame acoustic line signal.

14. An ultrasound signal processing method of performing transmission events of transmitting converging ultrasound beams to a subject by using an ultrasound probe having transducer elements, generating a sub-frame acoustic line signal for each of the transmission events based on signals acquired through reception of reflected ultrasound from the subject by the ultrasound probe, and synthesizing sub-frame acoustic line signals for the respective transmission events to generate a frame acoustic line signal, the ultrasound signal processing method comprising:

for each of the transmission events, shifting a transmission aperture including part of the transducer elements in a transducer element array direction in which the transducer elements are arrayed, and causing the ultrasound probe to transmit ultrasound beams to an ultrasound main irradiation area so that the ultrasound beams converge at a focal point defined by a position of the transmission aperture;

for each of the transmission events, generating sequences of receive signals for at least part of the transducer elements based on reflected ultrasound received by the ultrasound probe from the subject;

for each of the transmission events, setting a target area in the ultrasound main irradiation area, and performing delay-and-sum calculation with respect to the sequences of receive signals from measurement points located in the target area to generate a sub-frame acoustic line signal, wherein the target area is smaller than the ultrasound main irradiation area in a depth range shallower than a focal point of the ultrasound main irradiation area and delay-and-sum calculation is not performed on receive signals from measurement points in the ultrasound main irradiation area that are outside of the target area, the target area has a width in the transducer element array direction that decreases as the depth decreases, wherein the target area is defined by the ultrasound main irradiation area in a second depth range deeper than the depth range and the second depth range of the target area includes an area between the depth range and the focal point; and synthesizing sub-frame acoustic line signals for the transmission events to generate a frame acoustic line signal.

* * * * *